(12) United States Patent
Rhodes et al.

(10) Patent No.: US 11,648,153 B2
(45) Date of Patent: May 16, 2023

(54) ELASTICIZED ABSORBENT ARTICLES AND METHODS OF WEAKENING ELASTIC PORTIONS IN ELASTICIZED ABSORBENT ARTICLES

(71) Applicants: KIMBERLY-CLARK (CHINA) CO., LTD., Shanghai (CN); KIMBERLY-CLARK WORLD-WIDE, INC., Neenah, WI (US)

(72) Inventors: Brian K. Rhodes, Winneconne, WI (US); Timothy A. Thorson, Neenah, WI (US); Qingyuan Deng, Jiangning District of Nanjing (CN); Gregory J. Rajala, Neenah, WI (US); Rae Leonard Kirkwood, Greymouth (NZ)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 1014 days.

(21) Appl. No.: 16/340,433

(22) PCT Filed: Oct. 18, 2016

(86) PCT No.: PCT/CN2016/102380
§ 371 (c)(1),
(2) Date: Apr. 9, 2019

(87) PCT Pub. No.: WO2018/072084
PCT Pub. Date: Apr. 26, 2018

(65) Prior Publication Data
US 2019/0307613 A1    Oct. 10, 2019

(51) Int. Cl.
*A61F 13/15* (2006.01)
*A61F 13/49* (2006.01)
(Continued)

(52) U.S. Cl.
CPC .. *A61F 13/15593* (2013.01); *A61F 13/49011* (2013.01); *B29C 53/36* (2013.01);
(Continued)

(58) Field of Classification Search
CPC ..................... A61F 13/15593; B32B 38/0004
See application file for complete search history.

(56) References Cited

U.S. PATENT DOCUMENTS

| 3,793,133 A | 2/1974 | Beaudoin et al. |
| 5,622,581 A | 4/1997 | Ducker et al. |

(Continued)

FOREIGN PATENT DOCUMENTS

| CN | 101820840 A | 9/2010 |
| CN | 102271643 A | 12/2011 |

(Continued)

*Primary Examiner* — Philip C Tucker
*Assistant Examiner* — John Blades
(74) *Attorney, Agent, or Firm* — Kimberly-Clark Worldwide, Inc.

(57) ABSTRACT

Elasticized absorbent articles containing weakened elasticized portions and methods of manufacture are disclosed. A method comprises applying a first amount of adhesive to a first portion of at least one of the first web of material and the elastic strand, applying a second amount of adhesive to a second portion of at least one of the first web of material and the elastic strand, covering the elastic strand with either the first surface of the first web of material or a first surface of a second web of material to form an elasticized web. The elasticized web comprises a heavy bonding region and a light bonding region, wherein the heavy bonding region comprises a greater area density of adhesive than the light bond region. Finally, the method may further comprise partially weakening the waist panel elastic strand at least at one location within the second region.

10 Claims, 14 Drawing Sheets

(51) Int. Cl.
*B29C 53/36* (2006.01)
*B32B 37/02* (2006.01)
*B32B 37/12* (2006.01)
*B32B 37/14* (2006.01)
*B32B 37/20* (2006.01)
*B32B 38/00* (2006.01)
*B32B 38/04* (2006.01)

(52) U.S. Cl.
CPC .......... *B32B 37/02* (2013.01); *B32B 37/1292* (2013.01); *B32B 37/144* (2013.01); *B32B 37/206* (2013.01); *B32B 38/0004* (2013.01); *B32B 38/04* (2013.01); *B29C 2053/367* (2013.01); *B32B 2555/02* (2013.01)

(56) References Cited

U.S. PATENT DOCUMENTS

| | | |
|---|---|---|
| 6,602,238 B2 | 8/2003 | Takei et al. |
| 9,028,632 B2 | 5/2015 | Schneider et al. |
| 9,039,855 B2 | 5/2015 | Schneider et al. |
| 2002/0169432 A1 | 11/2002 | Fell et al. |
| 2005/0230037 A1 | 10/2005 | Jenquin et al. |
| 2011/0160692 A1 | 6/2011 | Wilkes et al. |
| 2013/0255460 A1 | 10/2013 | Schneider et al. |
| 2013/0255862 A1 | 10/2013 | Schneider et al. |
| 2013/0255865 A1 | 10/2013 | Brown et al. |
| 2013/0331250 A1* | 12/2013 | Coulombe ............... B26D 7/14 83/13 |
| 2016/0166441 A1 | 6/2016 | Adams et al. |
| 2017/0266057 A1* | 9/2017 | Eimann ............. A61F 13/15739 |

FOREIGN PATENT DOCUMENTS

| | | |
|---|---|---|
| CN | 203576752 U | 5/2014 |
| CN | 203576762 U | 5/2014 |
| CN | 104203177 A | 12/2014 |
| CN | 105682625 A | 6/2016 |
| EP | 1938777 B2 | 12/2015 |
| WO | 09042556 A1 | 4/2009 |
| WO | 16085491 A1 | 6/2016 |

* cited by examiner

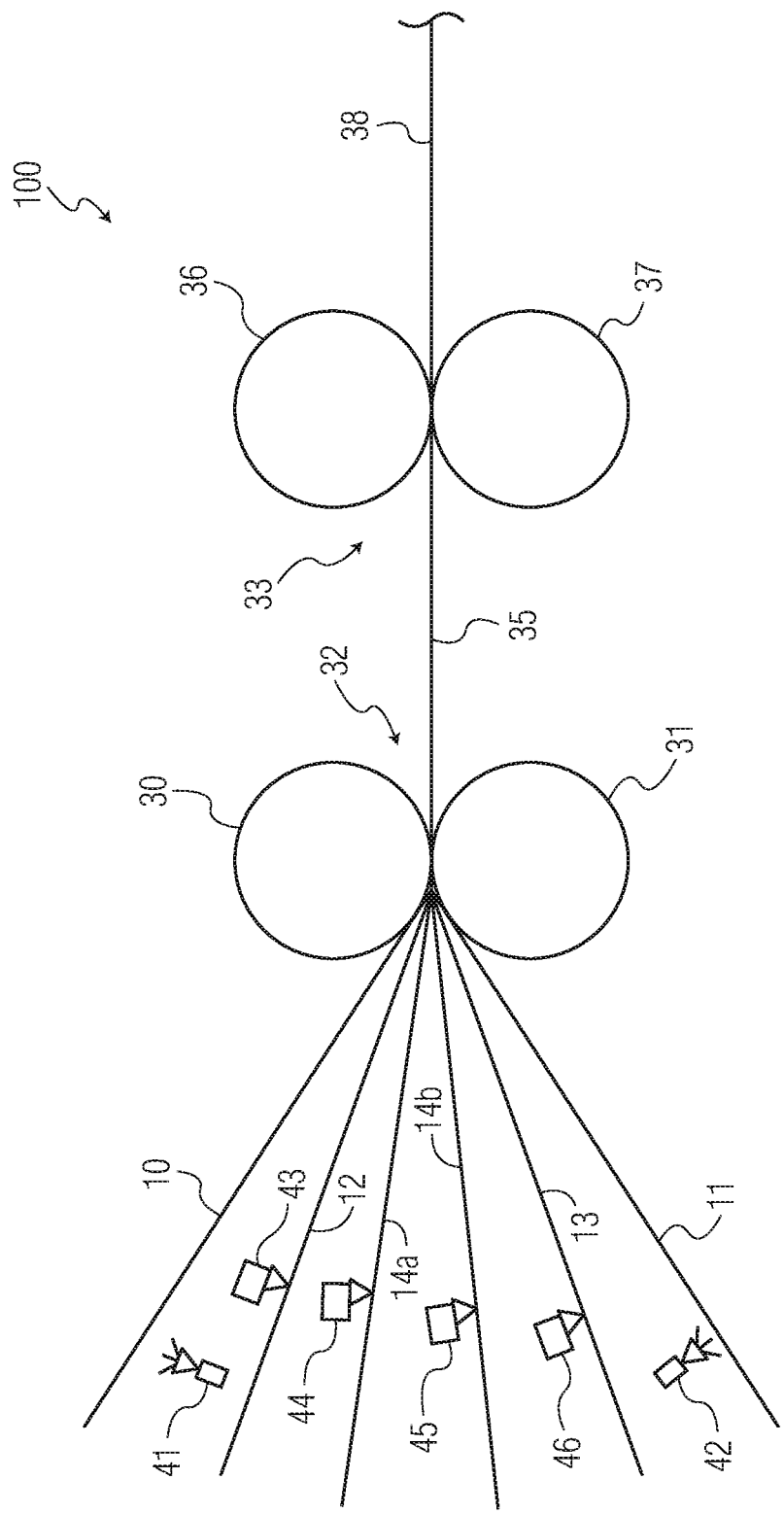

ELASTICIZED ABSORBENT ARTICLES AND METHODS OF WEAKENING ELASTIC PORTIONS IN ELASTICIZED ABSORBENT ARTICLES

TECHNICAL FIELD

The present disclosure is directed to elasticized absorbent articles, and more particularly to elasticized absorbent articles containing weakened elasticized portions.

BACKGROUND OF THE DISCLOSURE

One of the primary functions of personal care absorbent articles is to retain and absorb body exudates such as urine, fecal material, blood, and menses. Different varieties of disposable absorbent articles have different mechanisms for being retained on a wearer. For example, open diapers may have one or more Velcro-like attachment means for securing a rear portion of the diaper to the front portion of the diaper around the wearer's waist. Other absorbent articles such as diaper pants or adult pants may have a front waist panel that is permanently secured to a rear waist panel, with elastic strands running around the waist opening. Such absorbent articles are designed to be pulled on, with the elastic strands used to securely retain the article around the waist of the wearer. Both open diapers and absorbent pants may also have elastic strands running along the leg openings of the articles in order to secure the article around the legs of wearer.

Absorbent articles may be made in a variety of different manners. One group of general manufacturing processes are known as cross-direction (CD) processes. In CD processes, each of the front and rear waist panels travel during manufacturing in the machine direction, while the absorbent core is applied between the waist panels in the cross-machine direction. One of the beneficial features of these types of manufacturing processes is the ease of application of the elastic strands to the front and rear waist panels and along the leg openings, as the elastic strands may be applied in the direction of travel of the waist panel webs.

However, one detriment to these CD processes is that the elastic strands applied to the waist panel sections and around the leg openings may cause bunching of the absorbent core and/or ruffling of the outer cover web. Where the absorbent articles have printed graphics, those graphics may become distorted due to the bunching of the absorbent core and/or the ruffling of the outer cover in the region where the graphics are printed. Accordingly, de-elasticing or otherwise de-activating or reducing the elastic properties of the elastic strands at various locations on the absorbent article may reduce the bunching of the absorbent core and/or ruffling of the outer cover and reduce the distortion of any printed graphics.

SUMMARY OF THE DISCLOSURE

The disclosure is directed to several alternative designs, materials, and methods of manufacturing absorbent articles.

In a first illustrative example, a method of forming an elasticized portion of an absorbent article may comprise advancing a first web of material in a machine direction, advancing an elastic strand in the machine direction in a stretched state, applying a first amount of adhesive to a first portion of at least one of the first web of material and the elastic strand, applying a second amount of adhesive to a second portion of at least one of the first web of material and the elastic strand, placing the waist panel elastic strand on a first surface of the first web of material, covering the elastic strand with either the first surface of the first web of material or a first surface of a second web of material to form an elasticized web, the elasticized web comprising a heavy bond region and a light bond region, the heavy bond region comprising a greater area density of adhesive than the light bond region, and partially weakening the elastic strand at least at one location within the light bond region.

In a second illustrative example, the elastic strand of the first example may further comprise a plurality of micro-strands, and wherein partially weakening the elastic strand may comprise severing at least one of the plurality of micro-strands but less than all of the micro-strands.

In a third illustrative example, the step of partially weakening the elastic strand of any of the first and second examples may further comprise applying a compressive pressure of at least 0.250 MPa to the elastic strand without completely severing the elastic strand.

In a fourth illustrative example, any of the first through third examples may further comprise partially weakening the elastic strand at least at one location within the light bond region without forming an aperture in the first web of material or the second web of material.

In a fifth illustrative example, the step of partially weakening the elastic strand at least at one location within the light bond region of any of the first though fourth examples may further comprise partially weakening the elastic strand at least at five locations within the light bond region.

In a sixth illustrative example, after partially weakening the elastic strand at least at one location within the light bond region of any of the first though fifth examples, the partially weakened portion of elastic strand may elongate without forming ruffles in the first web of material.

In a seventh illustrative example, applying the first amount of adhesive to the first portion of at least one of the first web of material and the elastic strand of any of the first though sixth examples may comprise applying the first amount of adhesive to the first portion of the first web, and applying the second amount of adhesive to the second portion of at least one of the first web of material and the elastic strand may comprise applying the second amount of adhesive to the second portion of the first web.

In an eighth illustrative example, the elastic strand of any of the first through seventh examples may comprise a waist elastic strand.

In a ninth illustrative example, the elastic strand of any of the first through seventh examples may comprise a leg elastic strand.

In an tenth illustrative example, a method of forming an elastic waist panel for an absorbent article may comprise advancing a first web of material in a machine direction, advancing a plurality of waist panel elastic strands in the machine direction in a stretched state, applying a first adhesive continuously to a first subset of the plurality of waist panel elastic strands, applying the first adhesive intermittently to a second subset of the plurality of waist panel elastic strands, placing the plurality of waist panel elastic strands on a first surface of the first web of material, covering the plurality of waist panel elastic strands with either the first surface of the first web of material or a first surface of a second web of material to form an elasticized web, the elasticized web comprising a first region comprising the first adhesive and a second region without the first adhesive, and partially weakening each of the waist panel elastic strands of the second subset of waist panel elastic strands at least at one location on each of the waist panel elastic strands of the second subset of waist panel elastic strands within the second region.

In a eleventh illustrative example, the step of partially weakening each of the waist panel elastic strands of the second subset of waist panel elastic strands at least at one location on each of the waist panel elastic strands of the second subset of waist panel elastic strands within the second region of the tenth example may further comprise partially weakening each of the waist panel elastic strands of the second subset of waist panel elastic strands at least at five locations on each of the waist panel elastic strands of the second subset of waist panel elastic strands within the second region.

In a twelfth illustrative example, the step of partially weakening each of the waist panel elastic strands of the second subset of waist panel elastic strands any of the tenth though eleventh examples may further comprise applying a compressive pressure of at least 0.250 MPa without completely severing each of the waist panel elastic strands of the second subset of waist panel elastic strands.

In an thirteenth illustrative example, any of the tenth though twelfth examples may further comprise partially weakening each of the waist panel elastic strands of the second subset of waist panel elastic strands without cutting the first web of material or the second web of material.

In a fourteenth illustrative example, the step of partially weakening each of the waist panel elastic strands of the second subset of waist panel elastic strands at least at one location on each of the waist panel elastic strands of the second subset of waist panel elastic strands within the second region any of the tenth though thirteenth examples ay comprise partially weakening each of the waist panel elastic strands of the second subset of waist panel elastic strands at least at five locations on each of the waist panel elastic strands of the second subset of waist panel elastic strands within the second region.

In a fifteenth illustrative example, any of the tenth though fourteenth examples may further comprise applying a second adhesive to the first web of material, wherein the first region comprises both the first adhesive and the second adhesive and the second region comprises the second adhesive but not the first adhesive.

In a sixteenth illustrative example, a method of forming an elastic waist panel for an absorbent article may comprise advancing a first web of material in a machine direction, advancing a plurality of waist panel elastic strands in the machine direction in a stretched state, placing the plurality of waist panel elastic strands on a first surface of the first web of material, covering the plurality of waist panel elastic strands with either the first surface of the first web of material or a first surface of a second web of material to form an elasticized web, and partially weakening at least one of the plurality of waist panel elastic strands at least at one location on each of the at least one of the plurality of waist panel elastic strands.

In a seventeenth illustrative example, each of the plurality of waist panel elastic strands of the sixteenth example may comprise a plurality of micro-strands, and the step of partially weakening at least one of the plurality of waist panel elastic strands may comprise severing at least one of the plurality of micro-strands but less than all of the micro-strands of each of the at least one of the plurality of waist panel elastic strands.

In a eighteenth illustrative example, the step of partially weakening each of the at least one of the plurality of waist panel elastic strands any of the sixteenth through seventeenth examples may comprise applying a compressive pressure of at least 0.25 MPa without completely severing each of the at least one of the plurality of waist panel elastic strands.

In a nineteenth illustrative example, any of the sixteenth through eighteenth examples may further comprise partially weakening each of the at least one of the plurality of waist panel elastic strands without cutting the first web of material or the second web of material.

In a twentieth illustrative example, any of the sixteenth through nineteenth examples may further comprise applying adhesive to at least one of: one or more of the plurality of waist panel elastic strands; and the first web of material.

In a twenty-first illustrative example, the adhesive of the twentieth example may be applied in a manner that forms a zone within the elasticized web, wherein the adhesive is insufficient to securely bond the plurality of waist panel elastic strands to the first web of material within the zone, and wherein partially weakening the at least one of the plurality of waist panel elastic strands occurs within the zone.

In a twenty-second illustrative example, the adhesive of the twenty-first example may be applied in a manner such that the adhesive is sufficient to securely bond the plurality of waist panel elastic strands to the first web of material outside of the zone.

In a twenty-third illustrative example, an absorbent article may include a front waist region, a rear waist region, and a crotch region and may further comprise an absorbent assembly including a bodyside liner, an outer cover, and an absorbent body disposed between the bodyside liner and the outer cover, and the front waist region comprising an elasticized front waist panel and the rear waist region comprising an elasticized rear waist panel. Additionally, each of the elasticized front waist panel and elasticized rear waist panel may comprise a light bonding region and a heavy bonding region, the heavy bonding region comprising a greater area density of adhesive than the light bonding region, and the elasticized front waist panel and the elasticized rear waist panel each may comprise a plurality of composite elastic strands. Further, at least one composite elastic strand of each of the plurality of composite elastic strands of the elasticized front waist panel and the elasticized rear waist panel may comprise a partially weakened portion.

In a twenty-fourth illustrative example, each of the plurality of composite elastic strands of absorbent article of the twenty-third example may comprise a plurality of micro-strands, and each of the weakened portions of the composite elastic strands may comprise portions where at least one, but less than all, of the micro-strands have been severed.

In a twenty-fifth illustrative example, the at least one composite elastic strand of each of the plurality of composite elastic strands of the elasticized front waist panel and the elasticized rear waist panel of any of the twenty-third through twenty-fourth examples may comprise at least five partially weakened portions.

In a twenty-sixth illustrative example, the partially weakened portion of each of the least one composite elastic strand of each of the plurality of composite elastic strands of the elasticized front waist panel and the elasticized rear waist panel of any of the twenty-third through twenty-fifth examples may be located within the light bonding region.

In a twenty-seventh illustrative example, each of the elasticized front waist panel and the elasticized rear waist panel of any of the twenty-third through twenty-sixth examples may comprise a ruffled region and an un-ruffled region, wherein the weakened portions of the composite elastic strands are located within the un-ruffled region.

In a twenty-eighth illustrative example, the absorbent article of any of the twenty-third through twenty-seventh examples may further comprise a composite leg-elastic strand located within the crotch region, and wherein the composite leg-elastic strand comprises at least one partially weakened portion located within the crotch region.

The above summary of some example embodiments is not intended to describe each disclosed embodiment or every implementation of aspects of the disclosure.

BRIEF DESCRIPTION OF DRAWINGS

The aspects of the disclosure may be further understood in consideration of the following detailed description of various embodiments in connection with the accompanying drawings, in which:

FIGS. 1A-1C depict side views of system 100 for forming an elasticized absorbent article with weakened elastic portions, according to aspects of the present disclosure;

Figure 1B:
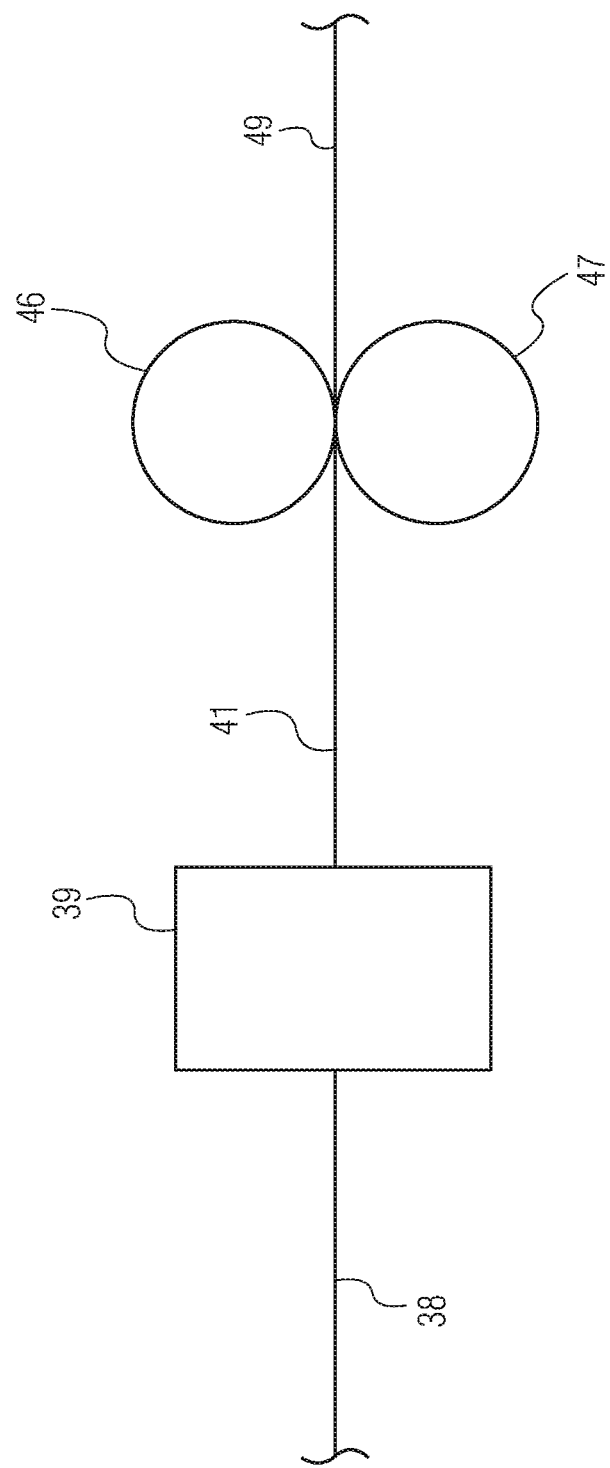

Repeat use of reference characters in the present specification and drawings is intended to represent the same or analogous features or elements of the disclosure. Additionally, while the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION OF THE DISCLOSURE

The present disclosure is generally directed towards elasticized absorbent articles that include weakened elastic portions. In some process for forming absorbent articles, composite elastic strands may be applied in a continuous manner such that the composite elastic strands run continuously through the absorbent article. The composite elastic strands may cause bunching of the absorbent core and/or ruffling of a garment facing web or outer cover. This bunching and/or ruffling may distort the absorbent article in undesirable ways. For instance, the absorbent core may not function optimally due to the bunching, or graphics printed on the garment facing web or outer cover may be distorted due to the ruffling. Accordingly, it may be desirable to de-elasticize portions of an absorbent article or weaken portions of the composite elastic strands within the absorbent article in order to reduce the bunching of the absorbent core and/or ruffling of the garment facing web. The present disclosure details methods for de-elasticizing portions of an absorbent article and weakening portions of the composite elastic strands within the absorbent article in order to reduce bunching of the absorbent core and/or ruffling of the garment facing web, and absorbent articles having de-elasticized portions or weakened portions of composite elastic strands.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

Definitions

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, training pants, youth pants, swim pants, feminine hygiene products, including, but not limited to, menstrual pads, incontinence products, medical garments, surgical pads and bandages, other personal care or health care garments, and the like without departing from the scope of the present disclosure.

The term "bonded" refers herein to the joining, adhering, connecting, attaching, or the like, of two elements. Two elements will be considered bonded together when they are joined, adhered, connected, attached, or the like, directly to one another or indirectly to one another, such as when each is directly bonded to intermediate elements. The bonding of one element to another can occur via continuous or intermittent bonds.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material which softens and which can be shaped when exposed to heat and which substantially returns to a non-softened condition when cooled.

The term "user" or "caregiver" refers herein to one who fits an absorbent article, such as, but not limited to, a diaper, training pant, youth pant, incontinent product, or other absorbent article about the wearer of one of these absorbent articles. A user and a wearer can be one and the same person.

Figure 1C:
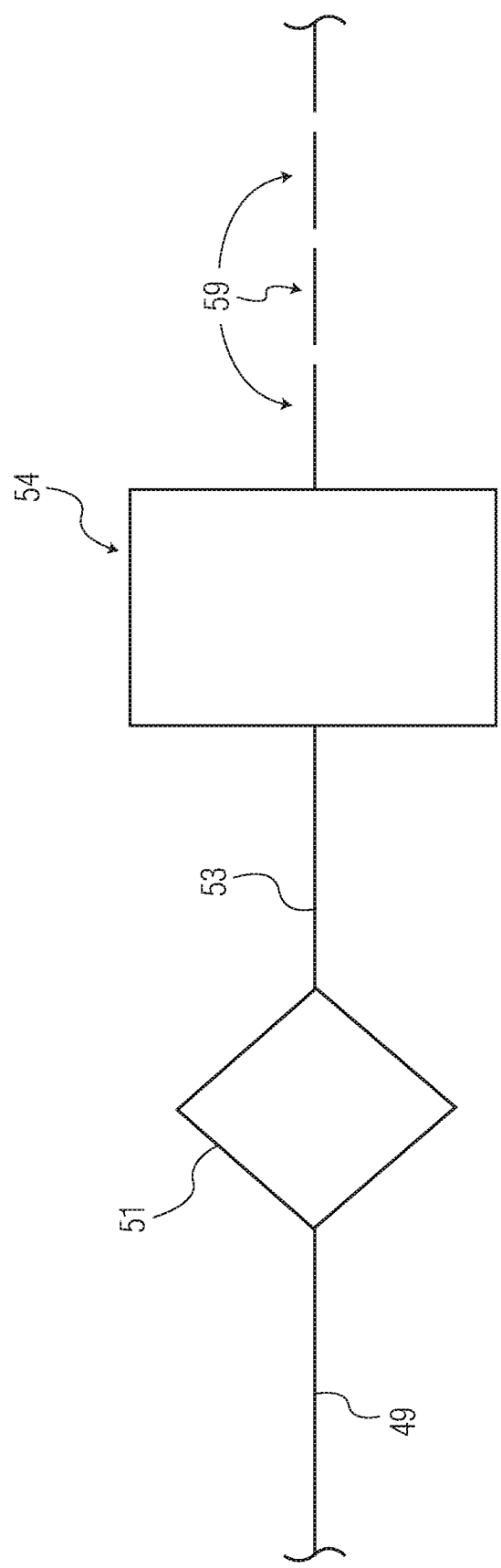

FIGS. 1A-1C depict side views of system 100 for forming an elasticized absorbent article with weakened elastic portions, according to aspects of the present disclosure. FIG. 1A specifically depicts a portion of system 100 comprising forming elasticized web 35 from multiple web materials and composite elastic strands 12-14b. Elasticized web 35 may form elasticized front and rear waist panels of an assembled absorbent article in order to securely retain the absorbent article around a waist of a wearer.

To form elasticized web 35, both body facing web 10 and garment facing web 11 may be fed into nip 32. A number of composite elastic strands, such as composite elastic strands 12-14b, may also be fed into nip 32 between body facing web 10 and garment facing web 11 to form elasticized web 35.

Body facing web 10 can be manufactured from a wide selection of materials, such as synthetic fibers (for example, polyester or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Various woven and non-woven fabrics can be used for body facing web 10. For example, body facing web 10 can include a woven fabric, a nonwoven fabric, a polymer film, a film-fabric laminate or the like, as well as combinations thereof. Examples of a nonwoven fabric can include spunbond fabric, meltblown fabric, coform fabric, carded web, bonded-carded web, bicomponent spunbond fabric, spunlace, or the like, as well as combinations thereof. Additionally, although only shown using a single line in FIG. 1A, body facing web 10 need not be a unitary layer structure. Thus, body facing web 10 can include more than one layer of fabrics, films, and/or webs, as well as combinations thereof. For example, body facing web 10 can include a support layer and a projection layer, and in some embodiments the two layers can be hydroentagled.

As one example, body facing web 10 can be composed of a meltblown or spunbond web of polyolefin fibers. Alternatively, body facing web 10 can be a bonded-carded web composed of natural and/or synthetic fibers. Body facing web 10 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entirety of body facing web 10 or it can be selectively applied to particular sections of body facing web 10.

In some embodiments, body facing web 10 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, and end-to-end may be used without departing from the scope of this disclosure. In at least one embodiment, body facing web 10 can be a spunbond substrate with a basis weight from about 10 or 12 to about 15 or 20 gsm. In a specific embodiment, body facing web 10 can be a 12 gsm spunbond-meltblown-spunbond substrate having 10% meltblown content applied between the two spunbond layers.

Although in some embodiments body facing web 10 may comprise generally non-elastomeric materials, in other embodiments body facing web 10 can include elastomeric materials. Accordingly, in some embodiments, body facing web 10 can be stretchable, and more suitably elastic. In further embodiments, body facing web 10 can be suitably stretchable and more suitably elastic in at least a lateral, or cross-, direction in relation to the general direction of travel of body facing web 10 through process 100. In other embodiments, body facing web 10 can be stretchable, and more suitably elastic, in both a cross-direction and a longitudinal, or machine-, direction in relation to the general direction of travel of body facing web 10 through process 100.

In some embodiments, garment facing web 11 and/or portions thereof can be breathable and/or liquid impermeable. Garment facing web 11 and/or portions thereof may further be elastic, stretchable, or non-stretchable. Garment facing web 11 may be constructed of a single layer, multiple layers, laminates, spunbond fabrics, films, meltblown fabrics, elastic netting, microporous webs, bonded-carded webs or foams provided by elastomeric or polymeric materials. In some embodiments, for example, garment facing web 11 can be constructed of a microporous polymeric film, such as polyethylene or polypropylene.

In at least some embodiments, garment facing web 11 can be a single layer of a liquid impermeable material, such as a polymeric film. In some of these embodiments, garment facing web 11 can be suitably stretchable, and more suitably elastic, in at least a lateral, or cross-, direction to the general direction of travel of garment facing web 11 through process 100. In other embodiments, garment facing web 11 can be stretchable, and more suitably elastic, in both the cross-direction and a longitudinal, or machine-, direction to the general direction of travel of garment facing web 11 through process 100. Garment facing web 11 can be a multi-layered laminate in which at least one of the layers is liquid impermeable.

Although shown only as a single line in FIG. 1A, in some specific embodiments garment facing web 11 can be a two layer construction, including an outer layer material and an inner layer material which can be bonded together such as by a laminate adhesive. Suitable laminate adhesives can be applied continuously or intermittently as beads, a spray, parallel swirls, or the like, but it is to be understood that the inner layer can be bonded to the outer layer by other bonding methods, including, but not limited to, ultrasonic bonds, thermal bonds, pressure bonds, or the like.

In embodiments where garment facing web 11 comprises a dual-layer structure, the outer layer of garment facing web 11 can be any suitable material and may be one that provides a generally cloth-like texture or appearance to the wearer. An example of such material can be a 100% polypropylene bonded-carded web with a diamond bond pattern available from Sandler A. G., Germany, such as 30 gsm Sawabond 4185® or equivalent. Another example of material suitable for use as an outer layer of garment facing web 11 can be a 20 gsm spunbond polypropylene non-woven web. The outer layer may also be constructed of the same materials from which body facing web 10 can be constructed as described above.

Whether garment facing web 11 comprises a single-layer or dual-layer structure, the single layer or the inner layer of the dual-layer structure may be liquid impermeable and can further be either vapor permeable (i.e., "breathable") or vapor impermeable. The liquid impermeable layer can be manufactured from a thin plastic film, microporous polymer film, or a non-woven material which has been coated or otherwise treated to impart a desired level of liquid impermeability. The liquid impermeable layer can inhibit liquid body exudates from leaking out of an absorbent article formed at least partially from garment facing web 11 and wetting articles, such as bed sheets and clothing, as well as the wearer and caregiver.

Composite elastic strand 12 and composite elastic strand 13 may form part of front and rear waist panels, respectively, of an absorbent article formed at least partially from elasticized web 35. Although only shown as single lines in FIG. 1A, composite elastic strands 12, 13 may comprise a plurality of elastic strands in order to form a wide elasticized area on the front and rear waist panels of an absorbent article. For instance, composite elastic strand 12 may represent between about 5 and about 30 individual elastic strands spaced from each other to form an elasticized front waist panel. Similarly, composite elastic strand 13 may represent between about 5 and about 30 individual elastic strands spaced from each other to form an elasticized rear waist panel. In various embodiments, the plurality of composite elastic strands represented by composite elastic strands 12, 13 may be spaced over an area of between about 3 inches (7.62 cm) and about 10 inches (25.4 cm) on the front waist panel or the rear waist panel, respectively.

Composite elastic strands 14a, 14b may represent composite leg elastic strands. For instance, an absorbent article formed at least partially from elasticized web 35 may include leg openings ringed at least partially by composite elastic strands, such as composite elastic strands 14a, 14b. As will be described later, as a part of process 100, portions of elasticized web 35 may be cut-out to form the leg openings of an absorbent article formed at least partially by elasticized web 35. In some embodiments, although shown only as single lines on FIG. 1A, composite elastic strands 14a, 14b may comprise a plurality of composite elastic strands. For example, in various embodiments, composite elastic strands 14a, 14b may represent between about 2 and about 7 discrete composite elastic strands.

Figure 2:
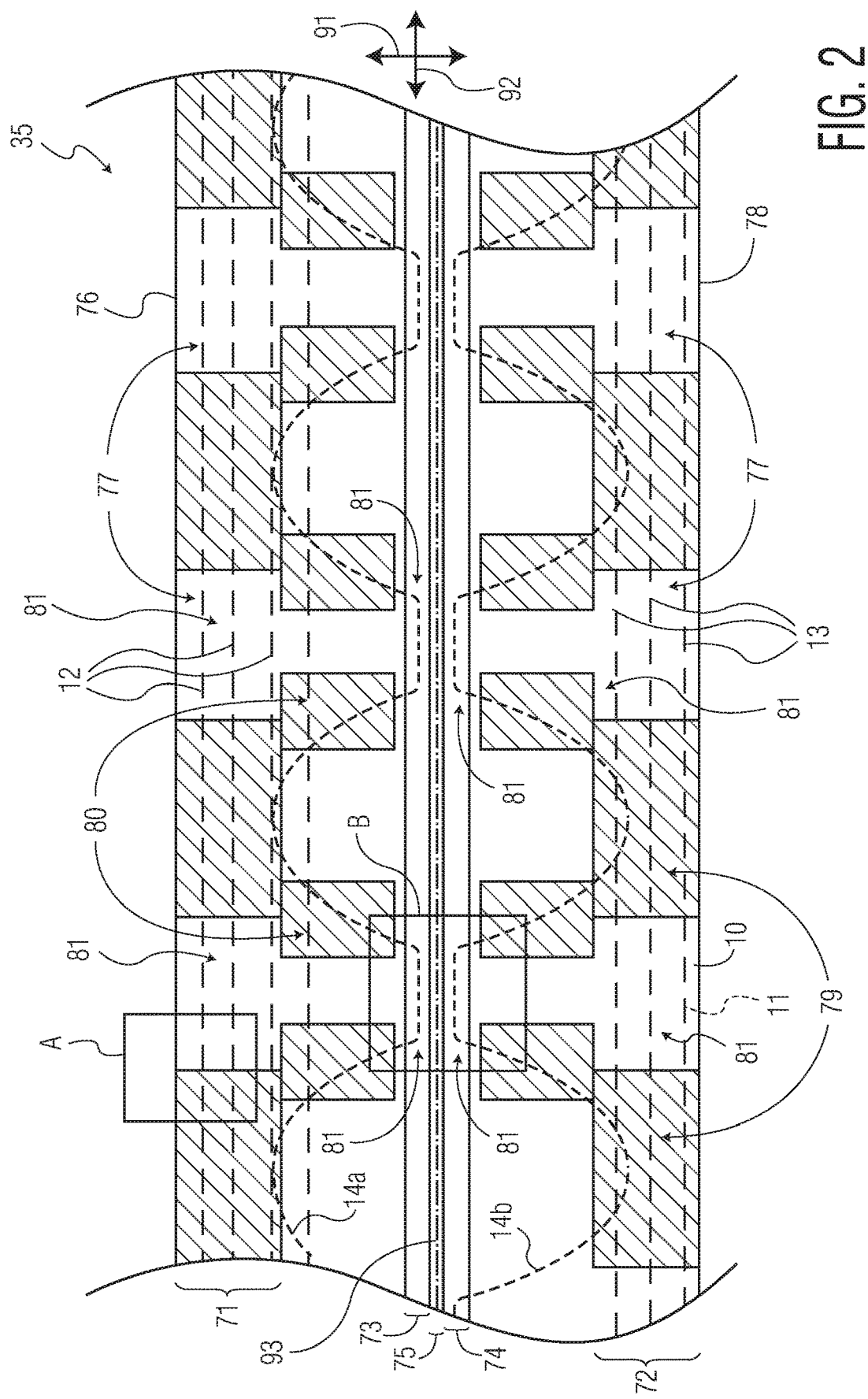
FIG. 2 depicts a plan view of an exemplary elasticized web after having gone through nip 32 as shown in FIG. 1A.

In at least some embodiments, composite elastic strands 14a, 14b may be fed into nip 32 at varying cross-machine direction positions in order to form an undulating pattern of composite elastic strands 14a, 14b within elasticized web 35. This undulating pattern, which can be seen more clearly in FIG. 2, may be formed by varying a position of a control bar or arm associated with each of composite elastic strands 14a, 14b. The undulating pattern of composite elastic strands 14a, 14b, as seen in FIG. 2, may coincide with a region of elasticized web 35 that is cut-out to form leg openings.

Composite elastic strands 12-14b can be formed from rubber or other elastomeric materials. Some suitable materials include Lycra® brand elastic filaments available from the DuPont Corporation. In some embodiments, composite elastic strands 12-14b are made of a Creora Spandex 940 decitex, which corresponds to a diameter of about 0.016 inches per strand. Additionally, each of the individual composite elastic strands 12-14b may be comprised of between about 10 and about 50 micro-strands that are wound together to form composite elastic strands 12-14b.

Another component of elasticized web 35 may comprise one or more adhesives in order to secure one or more of composite elastic strands 14a, 14b within elasticized web 35. In some embodiments, a facing adhesive may be applied to one or more of body facing web 10 and garment facing web 11, such as by adhesive sprayers 41 and/or 42. For instance, adhesive sprayers 41 and/or 42 may spray adhesive onto an inner surface of body facing web 10 and/or an inner surface of garment facing web 11, where the inner surfaces of body facing web 10 and garment facing web 11 are the surfaces that come into contact with composite elastic strands 12-14b.

In further embodiments, adhesive may be applied to one or more of composite elastic strands 12-14b through strand-coating applicators 43, 44, 45, and/or 46. One example strand-coating technology that may be used to coat one or more of composite elastic strands 12-14b with adhesive is Nordson SureWrap® adhesive technology. Various coating methods and techniques, including strand coating methods and techniques, are shown for example in U.S. Pat. Nos. 5,340,648, 5,501,756, 5,507,909, 6,077,375, 6,200,635, 6,235,137, 6,361,634, 6,561,430, 6,520,237, 6,582,518, 6,610,161, 6,613,146, 6,652,693, 6,719,846 and 6,737,102, all of which are hereby incorporated herein by reference in their entirety.

In some embodiments, adhesive applied to body facing web 10, garment facing web 11, and/or composite elastic strands 12-14b may be applied in a continuous manner and an intermittent manner to create differing bond regions within elasticized web 35. For instance, in some embodiments, a facing adhesive may be applied to either or both of body facing web 10 and garment facing web 11 in a continuous manner. In these embodiments, adhesive may be applied to one or more of composite elastic strands 12-14b in an intermittent manner. In this way, a light bond region may be created in elasticized web 35 where only the adhesive applied to body facing web 10 and/or garment facing web 11 is present and heavy bond regions where the adhesive applied to body facing web 10, garment facing web 11, and the one or more of composite elastic strands 12-14b is present.

In other embodiments, adhesive may be applied to one or more of composite elastic strands 12-14b in a continuous manner. In these embodiments, adhesive may be applied to either or both of body facing web 10 and garment facing web 11 in an intermittent manner to produce light bond regions and heavy bond regions in elasticized web 35. The different bond regions are described in more detail with respect to FIG. 2.

In still further embodiments, adhesive may be applied to only one of body facing web 10 and/or garment facing web 11 and one or more of composite elastic strands 12-14b. In such embodiments, the quantity of adhesive applied to body facing web 10 and/or garment facing web 11 or one or more of composite elastic strands 12-14b may vary. For instance, an area density of adhesive applied to body facing web 10 and/or garment facing web 11 or one or more of composite elastic strands 12-14b along a first length may be less than adhesive applied to body facing web 10 and/or garment facing web 11 or one or more of composite elastic strands 12-14b along a second portion. In this manner, light bond regions and heavy bond regions may be created while applying adhesive only to one of body facing web 10 and/or garment facing web 11 and one or more of composite elastic strands 12-14b. In at least some of these embodiments, the amount of applied adhesive may be varied through a continuous spray application to form the light bond regions and the heavy bond regions. In other embodiments, a first coating of adhesive may be applied continuously, while a second coating of adhesive may be applied intermittently on top of the first coating of adhesive to form the light bond regions and the heavy bond regions.

It should also be understood that in at least some embodiments where composite elastic strands are coated intermittently with adhesive, not all of the strands necessarily need to be coated intermittently. For instance, adhesive may be applied to continuously to either or both of body facing web 10 and garment facing web 11 in a continuous manner, to a first set of composite elastic strands 12-14b in a continuous manner, and to a second set of composite elastic strands 12-14b in an intermittent manner. In such embodiments, only the second set of composite elastic strands 12-14b may be partially weakened, while the composite elastic strands 12-14b of the first set are maintained.

After each of the components of elasticized web 35 are unwound, and adhesive is applied to one or more of the components, the components come together at nip 32. Nip roll 30 and nip roll 31 are positioned adjacent one another to compress body facing web 10, garment facing web 11, and composite elastic strands 12-14b as they enter nip 32. The pressure applied to the components of elasticized web 35 at nip 32 help to bond the components together into a single elasticized web, elasticized web 35, seen exiting nip 32 in FIG. 1A.

In at least some embodiments, composite elastic strands 12-14b are fed into nip 32 in a stretched state. For instance, composite elastic strands 12-14b may be elongated to between about 120% to about 180% of their unstretched states before being fed into nip 32. Because of how composite elastic strands 12-14b become adhered to body facing web 10 and garment facing web 11 due to the adhesive applied to body facing web 10, garment facing web 11, and/or composite elastic strands 12-14b, when composite elastic strands 12-14b are allowed to relax back to their unstretched states, composite elastic strands 12-14b may cause bunching of an absorbent core positioned across composite elastic strands 12-14b and/or ruffling of garment facing web 11. Bunching of the absorbent core can reduce the effectiveness of the absorbent article in retaining bodily discharges and ruffling of the garment facing web can reduce the visual appeal of the absorbent article by distorting graphics printed on garment facing web 11 or other parts of the absorbent article.

In order to reduce absorbent core bunching and/or ruffling of garment facing web 11, one or more of composite elastic strands 12-14b may be partially weakened in order to reduce the elasticity in specific portions of the absorbent article. Some methods of partially weakening one or more of composite elastic strands 12-14b includes passing elasticized web 35 through mutilation nip 33, which is comprised of anvil roll 37 and pattern roll 36.

Anvil roll 37 may comprise a cylindrical drum made of metal or another hard material and may have a relatively smooth surface. Pattern roll 36 may comprise a cylindrical drum similar to anvil roll 37, however pattern roll 36 may have a plurality of raised protrusions. As elasticized web 35 is fed into mutilation nip 33, one or more of the plurality of raised protrusions of pattern roll 36 may compress one or more of composite elastic strands 12-14b onto anvil roll 37. This compression may partially weaken the one or more composite elastic strands 12-14b by severing some, but not all, of the micro-strands comprising each of composite elastic strands 12-14b. This partial weakening produces a region on the one or more composite elastic strands 12-14b having less elasticity than non-weakened portions. In other embodiments, the compression may cause damage to composite elastic strands 12-14b other than severing at least some of the micro-strands but also results in a reduction in elasticity of the compressed portions of the one or more composite elastic strands 12-14b.

In general, the protrusions of pattern roll 36 may align with one or more of composite elastic strands 12-14b in light bond regions of elasticized web 35. In these light bond regions, composite elastic strands 12-14b may not be securely bonded to body facing web 10 and/or garment facing web 11. As the one or more composite elastic strands 12-14b become partially weakened in these light bond regions, the partially weakened portions of the one or more composite elastic strands 12-14b may elongate without pulling on body facing web 10 and/or garment facing web 11. In other words, the partially weakened portions of the one or more composite elastic strands 12-14b may slide between body facing web 10 and garment facing web 11. This results in regions of garment facing web 11 which are unsecured to composite elastic strands 12-14b and no longer bunch up due to composite elastic strands 12-14b.

This partial weakening may be distinct from severing one or more of composite elastic strands 12-14b. For instance, severing may comprise completely severing all of the micro-strands that comprise composite elastic strands 12-14b, as opposed to only severing less than all of the micro-strands. Additionally, severing one or more of composite elastic strands 12-14b may require protrusions on pattern roll 36 that have sharper points than those described in the present disclosure. Manufacturing and maintaining sharper protrusions may be result in higher production costs than the methods described herein. Severing the one or more of composite elastic strands 12-14b may further require severing one or more of body facing web 10 and garment facing web 11, which may be undesirable. Accordingly, the methods of the present disclosure around partially weakening the one or more composite elastic strands 12-14b have many benefits over completely severing the one or more composite elastic strands 12-14b in order to produce de-elasticized portions in an absorbent article.

As described above, elasticized web 35 may pass through mutilation nip 33 where one or more composite elastic strands 12-14b become partially weakened, resulting in partially weakened elasticized web 38, as shown in FIG. 1A. FIG. 1B depicts additional portions of system 100 including partially weakened elasticized web 38, absorbent core applicator 39, and cutting roll 46.

As seen in FIG. 1B, absorbent core applicator 39 may receive partially weakened elasticized web 38. Absorbent core applicator 39, shown generically, may, for example, receive a continuous stream of absorbent cores, either as discrete absorbent cores or as a continuous length of absorbent core material. In embodiments where absorbent core applicator 39 receives discrete absorbent cores, absorbent core applicator 39 may rotate and place the discrete absorbent cores onto partially weakened elasticized web 38 at spaced apart locations. Where absorbent core applicator 39 receives a continuous length of absorbent core material, absorbent core applicator 39 may cut a discrete portion out of the continuous length of absorbent core material and rotate the discrete portion before placing it onto partially weakened elasticized web 38. Absorbent core applicator 39 may continue this process, placing discrete absorbent cores at spaced apart locations on partially weakened elasticized web 38.

As partially weakened elasticized web 38 comes out of absorbent core applicator 39 with absorbent cores positioned thereon, the web may be called composite web 41. As further seen in FIG. 1B, composite web 41 is then fed to anvil roll 47 and knife roll 46 in order to cut-out pieces of composite web 41 to form leg openings for individual absorbent articles. Knife roll 46 may have a raised sharp edge traversing the surface of knife roll 46 in a pre-defined pattern, and may have multiple such patterns spaced around the circumference of the knife roll 46. These multiple spaced apart patterns operate to cut-out multiple portions of composite web 41 at spaced apart locations in order to form leg openings at pre-defined spacings. One specific implementation of a knife roll and leg hole pattern that may be used to form leg-openings in composite web 41 is described in U.S.

Pat. No. 8,622,983, titled "Method of incorporating leg elastics in a pant-like disposable absorbent garment, and garment made thereby", which is hereby incorporated herein by reference in its entirety. However, it should be understood that any particular cut-out shape may be used to form leg-openings, and other methods of forming these leg openings may be used without departing from the scope of this disclosure.

Figure 10:
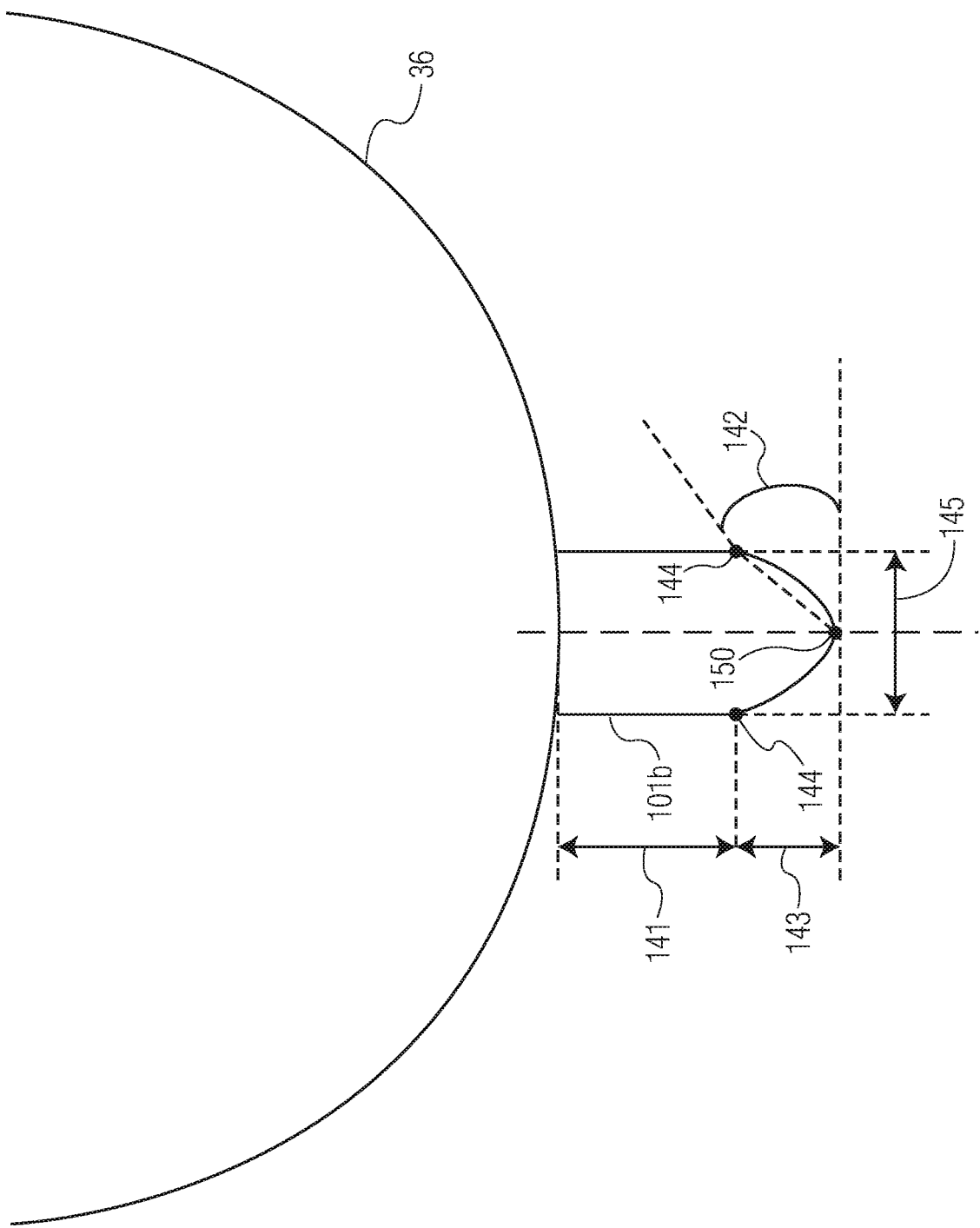
FIG. 10 is a side-view of another exemplary protrusion of the pattern roll of FIG. 5.

As composite web 41 moves away from anvil roll 47 and knife roll 46, the cut composite web may be called cut web 49, as seen in FIG. 1B. FIG. 10 depicts cut web 49 entering folder 51, which may fold cut web 49 in half, bringing a rear waist region of cut web 41 proximate a front waist region. The distinct front and rear waist regions may be seen more clearly with respect to FIG. 2, depicting front waist region 71 and rear waist region 72. Again, U.S. Pat. No. 8,622,983 describes an exemplary folding mechanism and technique that may be used to fold cut web 41 to bring one waist region proximate to another waist region. It should also be understood that any particular folding method may be used without departing from the scope of this disclosure.

As seen in FIG. 10, folded web 53 may then be fed to bonding and cutting module 54. Bonding and cutting module 54 may bond portions of folded web 53 together at discrete, spaced apart locations. For instance, as folded web 53 enters bonding and cutting module 54 with rear waist panel region 72 (shown in FIG. 2) of folded web 53 proximate front waist region 71 of folded web 53, bonding and cutting module 54 may form discrete, spaced apart bond strips securing the rear and front waist regions 72, 71 together. Bonding and cutting module 54 may form the discrete, spaced apart bond strips using adhesive, heat, ultrasonics, pressure, or any other bonding techniques. These bond strips eventually form lateral edges on individual absorbent articles.

After these discrete, spaced apart bond regions have been formed, bonding and cutting module 54 cuts through folded web 53, including through both the rear and front waist regions 72, 71 of folded web 53. In some embodiments, bonding and cutting module 54 may comprise a knife and anvil roll in order to cut through folded web 53. This cut produces discrete absorbent articles 59, as shown in FIG. 10, with sealed lateral edges. Discrete absorbent articles 59 are elasticized absorbent articles and include weakened elastic portions.

The following description describes elasticized web 35 and the process of forming partially weakened portions in composite elastic strands of elasticized web 35 in more detail. It should be understood that this description is generally independent of the process described above for forming absorbent articles. Indeed, any other processes that are known in the art to form elasticized absorbent articles in a CD process using an elasticized web may be used with the elasticized web 35 including weakened elastic portions in order to form elasticized absorbent articles including weakened elastic portions.

FIG. 2 is a plan view of elasticized web 35 depicting locations of light bond regions, heavy bond regions, and composite elastic strands 12-14b. Specifically, elasticized web 35 may include front waist region 71 having front waist edge 76, which can include composite elastic strands 12. Again, although only four individual composite elastic strands 12 are shown in FIG. 2 as forming front waist region 71, as described previously, in various embodiments the number of composite elastic strands 12 that comprise front waist region 71 may be anywhere between about 5 and about 30. Additionally as can be seen, front waist region 71 also includes alternating regions of light bond regions 77 and heavy bond regions 79.

As described previously, light bond regions 77 and heavy bond regions 79 may be formed in a number of different ways, for instance by continuous and intermittent application of adhesive to one or more of body facing web 10, garment facing web 11, and composite elastic strands 12-14b. One previously described example included spraying an adhesive continuously over one or both of body facing web 10 and garment facing web 11 while intermittently coating one or more of composite elastic strands 12-14b. In such embodiments light bond regions 77 may comprise the regions of elasticized web 35 where only the continuously applied adhesive is located. Although arrows 77 point generally to regions proximate front waist edge 76 and rear waist edge 78, light bond regions 77 extend throughout elasticized web 35 except as broken up by heavy bond regions 79 and/or tunnel adhesive zones 73, 74. Heavy bond regions 79, then, may comprise regions where both the continuously sprayed adhesive and the intermittently applied adhesive are present. More specifically, heavy bond regions 79 may be general regions defined by an extent of the intermittently applied adhesive. For example, in some embodiments the cross-machine direction 91 spacing between each composite elastic strand, such as composite elastic strands 12 of front waist region 71, may be greater than the cross-machine direction 91 spread of the intermittently applied adhesive. However, a heavy bond region 79 may be defined as the entire region of elasticized web 35 extending from the coated composite elastic strand 12 most distal from front waist edge 76 within front waist region 71 to the coated composite elastic strand 12 most proximal to front waist edge 76 within front waist region 71 and having machine direction 92 edges where the intermittently applied adhesive was not applied.

The end result of whatever chosen method may produce light bond regions 77 have an amount of adhesive of between about 0.01 gsm and about 0.03 gsm, while heavy bond regions 79 may have an amount of adhesive of between about 0.50 gsm and about 2.00 gsm. In some embodiments, light bond regions 77 and heavy bond regions 79 may comprise a single type of adhesive present in different quantities. In other embodiments, light bond regions 77 may comprise only a single type of adhesive, whereas heavy bond regions 79 may comprise two separate types of adhesives.

Although the specific widths and lengths of light bond regions 77 and heavy bond regions 79 may vary in different embodiments, some sizes of light bond regions 77 that may be suitable in some embodiments include regions 77 having lengths in the machine direction 92 between about 4.5 inches (11.5 cm) and about 5.3 inches (13.5 cm) and widths in the cross-machine direction 91 between about 3.9 inches (10 cm) and about 5.0 inches (12.5 cm). Some sizes of heavy bond regions 79 that may be suitable in some embodiments include regions 79 having lengths in the machine direction 92 between about 4.7 inches (12 cm) and about 5.9 inches (15 cm) and widths in the cross-machine direction 91 between about 1.5 inches (4.0 cm) and about 2.7 inches (7.0 cm).

It should be understood that, although the general shapes of heavy bond regions 79 are shown as rectangular, in various embodiments the specific shape of regions 77, 79 may be any suitable shape without departing from the scope of the present disclosure. Additionally, although each of regions 77, 79 depicted in FIG. 2 include abutting front waist edge 76, this is not necessary in all embodiments. The specific placement of regions 77, 79 within front waist region 71 may vary between different embodiments, and in at least some embodiments edges of regions 77, 79 proximate front waist edge 76 may be spaced from front waist edge 76. In some more specific embodiments it is the case that one or more composite elastic strands 12 proximate front waist region edge 76 may be continuously coated in adhesive even while other composite elastic strands 12 are intermittently coated in adhesive. In such embodiments, elasticized web 35 may include a heavy bond region 79 region proximate front waist edge 76 which extends along the machine direction 92 of elasticized web 35. Accordingly, in these embodiments, light bond regions 77 may be spaced from front waist edge 76 by the heavy bond region 79 extending in the machine direction 92 proximate front waist edge 76.

FIG. 2 additionally depicts rear waist region 72 having rear waist edge 78, including composite elastic strands 13. Additionally, although only three individual composite elastic strands 12 are shown in FIG. 2 as forming rear waist region 72, as described previously, in various embodiments the number of composite elastic strands 13 that comprise rear waist region 72 may be anywhere between about 5 and about 30. Like with front waist region 71, rear waist region 72 may also have alternating light bond regions 77 and heavy bond regions 79. The shapes and sizes of light and heavy bond regions 77, 79 of rear waist region 72 may be generally similar to those described with respect to front waist region 71. Additionally, in at least some embodiments, the alternating light bond regions 77 and heavy bond regions 79 of both front waist region 71 and rear waist region 72 may generally align in the machine direction 92 of elasticized web 35.

Elasticized web 35 can be seen further comprising composite elastic strands 14a, 14b traversing elasticized web 35 in an undulating pattern in order to form leg-elastics of an elasticized absorbent article formed at least partially from elasticized web 35. In some of these embodiments, composite elastic strands 14a, 14b may be symmetrically opposite in how they traverse across elasticized web 35. However, in other embodiments, as in the embodiment of FIG. 2, composite elastic strands 14a, 14b may have different undulating patterns. As composite elastic strands 14a, 14b undulate throughout elasticized web 35, composite elastic strands 14a, 14b may generally undulate throughout a crotch region of elasticized web 35 that is defined between front waist region 71 and rear waist region 72. However, in some embodiments, some portions of composite elastic strands 14a, 14b may enter into front waist region 71 and/or rear waist region 72.

In some embodiments, in addition to light bond regions 77 and heavy bond regions 79, elasticized web 35 may optionally further include anchor adhesive zones 80. Anchor adhesive zones 80 may be zones that include additional adhesive in comparison to the amounts of adhesive within light bond regions 77, and in some cases may include an amount of adhesive in the ranges specified for heavy bond regions 79. As can be seen in FIG. 2, anchor adhesive zones 80 may generally extend throughout the crotch region of elasticized web 35, which is defined as the region between front waist region 71 and rear waist region 72. Anchor adhesive zones 80 may generally comprise a first edge located proximate central axis 93 of elasticized web 35, and may extend toward either front waist region 71 or rear waist region 72. In some embodiments, anchor adhesive zones 80 extend from central axis 93 all the way to front waist region 71 or rear waist region 72. However, in other embodiments, there may be some small spacing between anchor adhesive zones 80 and central axis 93 and/or regions 71, 72. In still other embodiments, anchor adhesive zones 80 may extend completely between front waist region 71 and rear waist region 72, such that anchor adhesive zones 80 extend over central axis 93.

As can be seen in FIG. 2, anchor adhesive zones 80 may at least cover portions of composite elastic strands 14a, 14b. Accordingly, part of the function of anchor adhesive zones 80 is to ensure adequate bonding of composite elastic strands 14a, 14b with body facing web 10 and/or garment facing web 11 in order to ensure that composite elastic strands 14a, 14b are held securely in place at least within those anchor regions. In some embodiments, composite elastic strands 14a, 14b may be coated with adhesive in an intermittent fashion in order to form such anchor adhesive zones 80. In other embodiments, the continuous application of adhesive to body facing web 10 and/or garment facing web 11 may be applied more heavily in anchor adhesive zones 80 than in other regions of elasticized web 35, or a second spray application of adhesive may be incorporated and targeted to only spray within anchor adhesive zones 80 in order to achieve a higher area density of adhesive within anchor adhesive zones 80. Although specific suitable dimensions for anchor adhesive zones 80 may vary in different embodiments, in at least some embodiments suitable machine direction 92 lengths for an individual anchor zone 80 may be between about 7.8 inches (20 cm) and about 12.6 inches (32 cm).

In other embodiments, elasticized web 35 may optionally include tunnel adhesive zones 73, 74. In some embodiments, elasticized web may include both elasticized web 35 and anchor adhesive zones 80. Generally, tunnel adhesive zones 73, 74 may comprise regions of elasticized web 35 that are devoid of adhesive, for instance either the intermittently applied adhesive or the continuously applied adhesive. In some of these embodiments, tunnel adhesive zone 73 may be located proximate central axis 93 on a first side of central axis 93, while tunnel adhesive zone 74 may be located proximate central axis on a second side of central axis 93. Accordingly, in such embodiments, there may be an intermediate zone 75 between tunnel adhesive zones 73, 74. Intermediate zone 75 may include adhesive, such as the continuously applied adhesive. Generally, tunnel adhesive zones 73, 74 may be continuous zones that extend throughout elasticized web 35 in the machine direction 92, although this is not necessary. Additionally, tunnel adhesive zones 73, 74 may coincide with composite elastic strands 14a, 14b, respectively, along one or more portions of composite elastic strands 14a, 14b. In other embodiments, however, tunnel adhesive zones 73, 74 may instead comprise a single zone that crosses central axis 93, and coincide with both of composite elastic strands 14a, 14b along one or more portions of composite elastic strands 14a, 14b.

One other feature that may be seen in FIG. 2 are mutilation zones 81. Mutilation zones 81 comprise regions of elasticized web 35 where composite elastic strands 12-14b may become partially weakened according to aspects of the present disclosure. For instance, pattern roll 36 may comprise a plurality of protrusions that align with mutilation zones 81 of elasticized web 35 such that as elasticized web 35 is fed into mutilation nip 33, the plurality of protrusions align with one or more of composite elastic strands 12-14b within mutilation zones 81. In some embodiments, pattern roll may comprise protrusions that align with each of composite elastic strands 12-14b within mutilation zones 81, while in other embodiments, pattern roll may comprise protrusions that align with only some of composite elastic strands 12-14b within mutilation zones 81. Accordingly, in some embodiments, each of composite elastic strands 12-14b within each mutilation zone 81 may become partially weakened, while in other embodiments only some of composite elastic strands 12-14b within each mutilation zones may become partially weakened. In still other embodiments, each of composite elastic strands 12-14b within some mutilation zones 81 may become partially weakened while in other mutilation zones 81, only some of composite elastic strands 12-14b become partially weakened. In additional contemplated embodiments, only some of composite elastic strands 12-13 may become partially weakened, or only some of composite elastic strands 14a, 14b may become partially weakened.

As can be seen in FIG. 2, mutilation zones 81 overlap light bond regions 77 of elasticized web 35. Accordingly, the composite elastic strands 12-14b which are partially weakened as they pass through nip 33 are generally present in light bond regions 77. As described previously, the amount of adhesive within light bond regions 77 may be not enough to securely hold composite elastic strands 12-14b in place after the partial weakening. Accordingly, after the partial weakening, the portions of composite elastic strands 12-14b that where partially weakened may elongate between body facing web 10 and/or garment facing web 11 without pulling on body facing web 10 and/or garment facing web 11, thereby reducing the ruffling of body facing web 10 and/or garment facing web 11 and/or bunching of absorbent cores subsequently placed on elasticized web 35.

In some embodiments, mutilation zones 81 may only comprise zones associated with composite elastic strands 12, 13 of front waist region 71 and rear waist region 72. For example, in some embodiments only one or more of composite elastic strands 12, 13 may become partially weakened. In other embodiments, mutilation zones 81 may only comprise zones associated with composite elastic strands 14a, 14b. In still other embodiments, mutilation zones 81 may comprise zones associated with both composite elastic strands 12, 13 of front waist region 71 and rear waist region 72 and zones associated with composite elastic strands 14a, 14b.

Figure 3A:
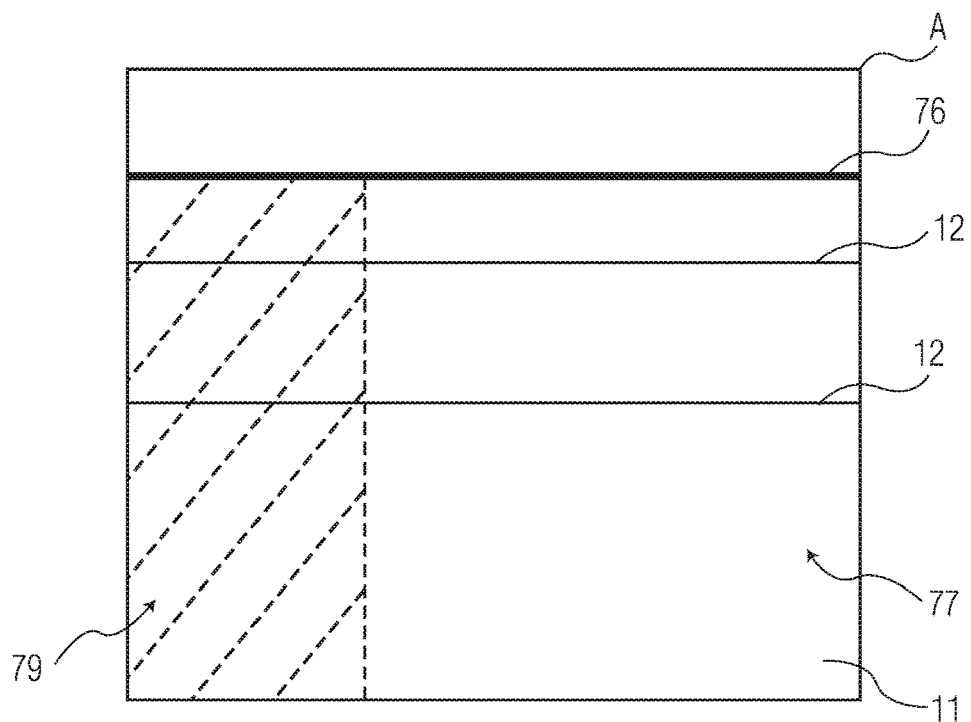
FIG. 3A is a plan view of a first exemplary front waist region portion of the elasticized web of FIG. 2, detailing composite elastic strands and light bond and heavy bond regions.

FIG. 3A depicts an example close-up of region A of FIG. 2 with body facing web 10 removed to show composite elastic strands 12 exposed. The area highlighted in FIG. 3A depicts a portion of a heavy bond region 79, shown by dashed shading lines, a portion of a light bond region 77, the region of FIG. 3A without dashed shading lines, and composite elastic strands 12 traversing through both regions 77, 79. In the embodiment of FIG. 3A, light bond region 77 may be formed by spraying a continuous application of adhesive onto body facing web 10 and/or garment facing web 11. Accordingly, the continuously sprayed adhesive may be present all over garment facing web 11 shown in FIG. 3A, e.g. throughout both light bond region 77 and heavy bond region 79. Heavy bond region 79 may be formed by spraying additional adhesive onto body facing web 10 and/or garment facing web 11 in an intermittent manner. Accordingly, heavy bond region 79 may comprise an area having a higher area density of adhesive than light bond region 77.

Figure 3B:
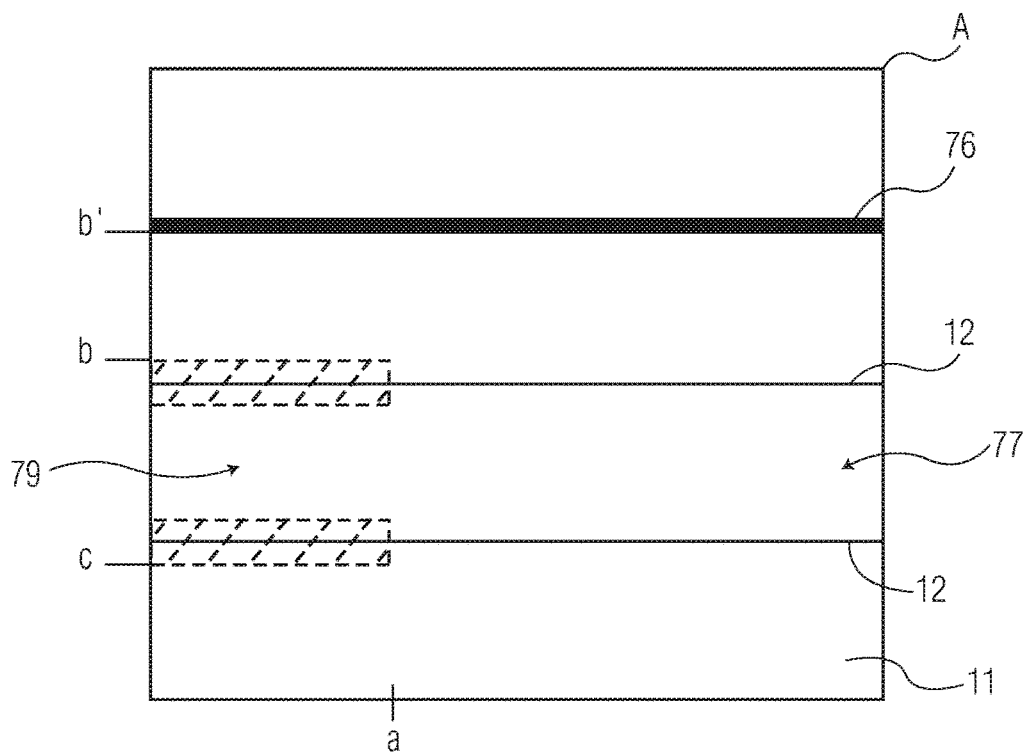
FIG. 3B is a plan view of a second exemplary front waist region portion of the elasticized web of FIG. 2, detailing composite elastic strands and light bond and heavy bond regions.

FIG. 3B depicts another example close-up of region A of FIG. 2 with body facing web 10 removed to show composite elastic strands 12 exposed. The area highlighted in FIG. 3B depicts a portion of a heavy bond region 79, and a portion of a light bond region 77. In the embodiment of FIG. 3B, light bond region 77 may be formed by spraying a continuous application of adhesive onto body facing web 10 and/or garment facing web 11. Accordingly, the continuously sprayed adhesive may be present all over garment facing web 11 shown in FIG. 3B, e.g. throughout both light bond region 77 and heavy bond region 79. Heavy bond region 79, in an alternative method to that described with respect to FIG. 3A, may be formed by coating composite elastic strands 12 with adhesive in an intermittent fashion. The dashed shading lines shown in FIG. 3B depict an extent of the coating adhesive on garment facing web 11 that was applied to composite elastic strands 12.

In the embodiment of FIG. 3B, heavy bond region 79 may be defined by the extent of the intermittently applied coating adhesive as opposed to being defined by specific areas where both a continuously applied adhesive and an intermittently applied adhesive is present. For example, in the embodiment of FIG. 3B, heavy bond region 79 may comprise the region bounded laterally by the extent of the intermittently applied adhesive, as denoted by position mark a. Additionally, heavy bond region 79 may be bounded longitudinally by the distal most longitudinal extent from waist edge 76 of the intermittently applied adhesive around the distal most composite coated elastic strand 12 from front waist edge 76, as denoted by position mark c. Further, heavy bond region 79 may be bounded longitudinally by the proximal most longitudinal position of the intermittently applied adhesive to waist edge 76 of the proximal most coated composite elastic strand 12 to front waist edge 76, as denoted by position mark b. However, where the proximal most coated composite elastic strand 12 to front waist edge 76 is the also the proximal most composite elastic strand 12 to front waist edge 76, the longitudinal boundary proximate to front waist edge 76 may instead just be waist edge 76.

Figure 4A:
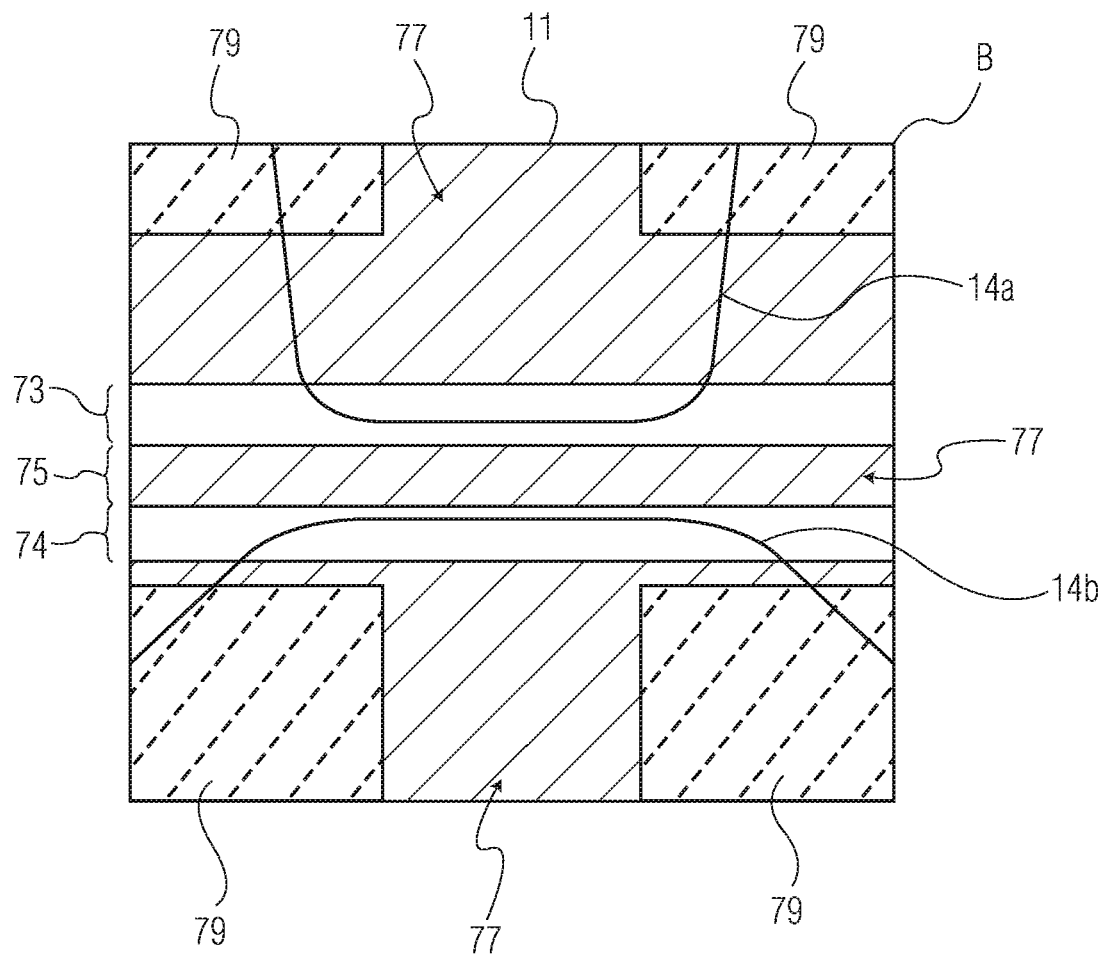
FIG. 4A is a plan view of a first exemplary crotch region portion of the elasticized web of FIG. 2, detailing composite elastic strands and light bond and heavy bond regions.

FIG. 4A depicts an example close-up of region B of FIG. 2 with body facing web 10 removed to show composite elastic strands 14a-b exposed. The area highlighted in FIG. 4A depicts portions of heavy bond regions 79, shown by dashed shading lines, portions of light bond regions 77, the region of FIG. 4A with solid shading lines, and composite elastic strands 14a-b traversing through regions 77, 79. In the embodiment of FIG. 4A, light bond regions 77 may be formed by spraying a continuous application of adhesive onto body facing web 10 and/or garment facing web 11. Accordingly, the continuously sprayed adhesive may be present all over garment facing web 11 shown in FIG. 4A, e.g. throughout both light bond regions 77 and heavy bond regions 79. Heavy bond regions 79 may be formed by spraying additional adhesive onto body facing web 10 and/or garment facing web 11 in an intermittent manner. Accordingly, heavy bond regions 79 may comprise an area having a higher area density of adhesive than light bond regions 77. FIG. 4A additionally depicts tunnel adhesive zones 73, 74 which are devoid of adhesive. For instance, no continuously applied adhesive may be applied in tunnel adhesive zones 73, 74, or a masking member may be placed so as to block application of adhesive sprayed at tunnel adhesive zones 73, 74. Again, these tunnel adhesive zones 73, 74 are optional features of elasticized web 35.

Figure 4B:
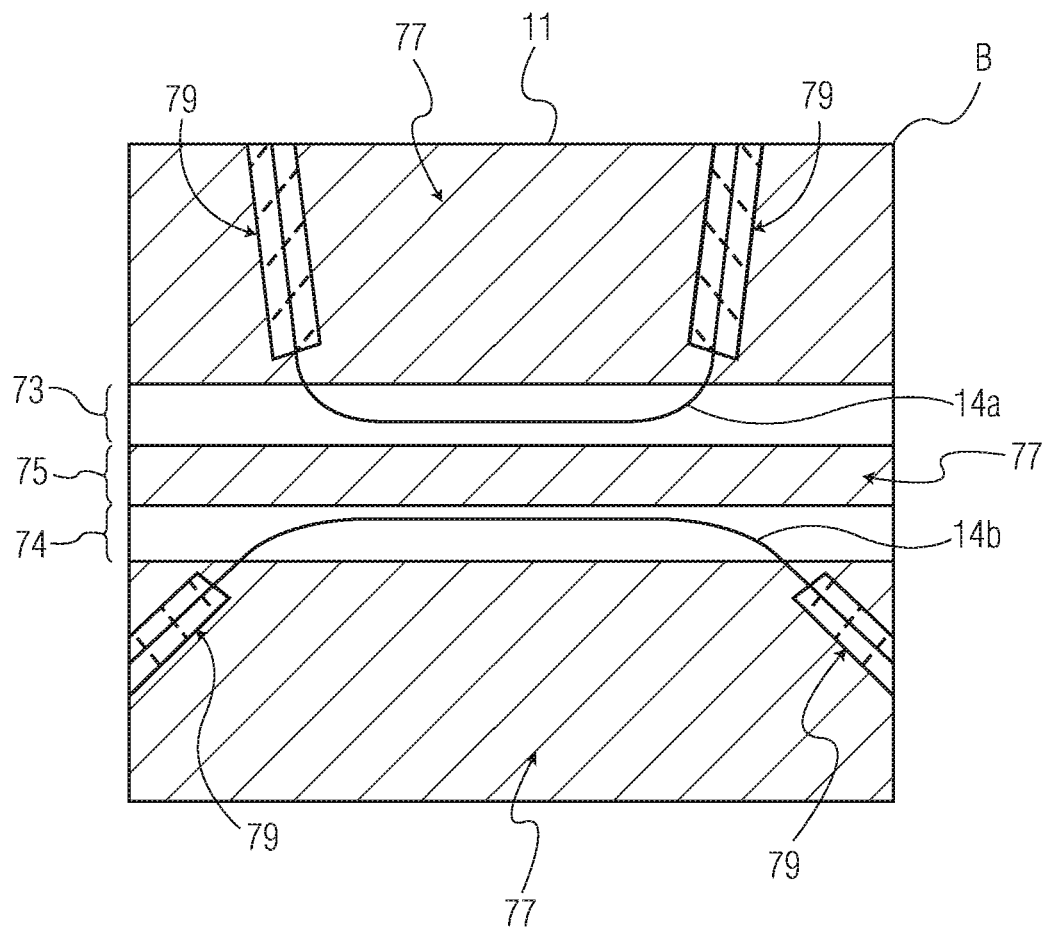
FIG. 4B is a plan view of a second exemplary crotch region portion of the elasticized web of FIG. 2, detailing composite elastic strands and light bond and heavy bond regions.

FIG. 4B depicts another example close-up of region B of FIG. 2 with body facing web 10 removed to show composite elastic strands 14a-b exposed. The area highlighted in FIG. 4B depicts portions of heavy bond regions 79, and portions of light bond regions 77. In the embodiment of FIG. 4B, light bond regions 77 may be formed by spraying a continuous application of adhesive onto body facing web 10 and/or garment facing web 11. Accordingly, the continuously sprayed adhesive may be present all over garment facing web 11 shown in FIG. 3B, e.g. throughout both light bond regions 77 and heavy bond regions 79. Heavy bond regions 79, in an alternative method to that described with respect to FIG. 4A, may be formed by coating composite elastic strands 14*a*-*b* with adhesive in an intermittent fashion. The dashed shading lines shown in FIG. 4B depict an extent of the coating adhesive on garment facing web 11 that was applied to composite elastic strands 14*a*-*b*. Heavy bond regions 79 associated with composite elastic strands 14*a*-*b* may be the regions of elasticized web 35 that contain both the continuously applied adhesive and the intermittently applied coating adhesive applied intermittently to composite elastic strands 14*a*-*b*. Again, FIG. 4B additionally depicts tunnel adhesive zones 73, 74 which are devious of adhesive, which are optional features of elasticized web 35.

Figure 5:
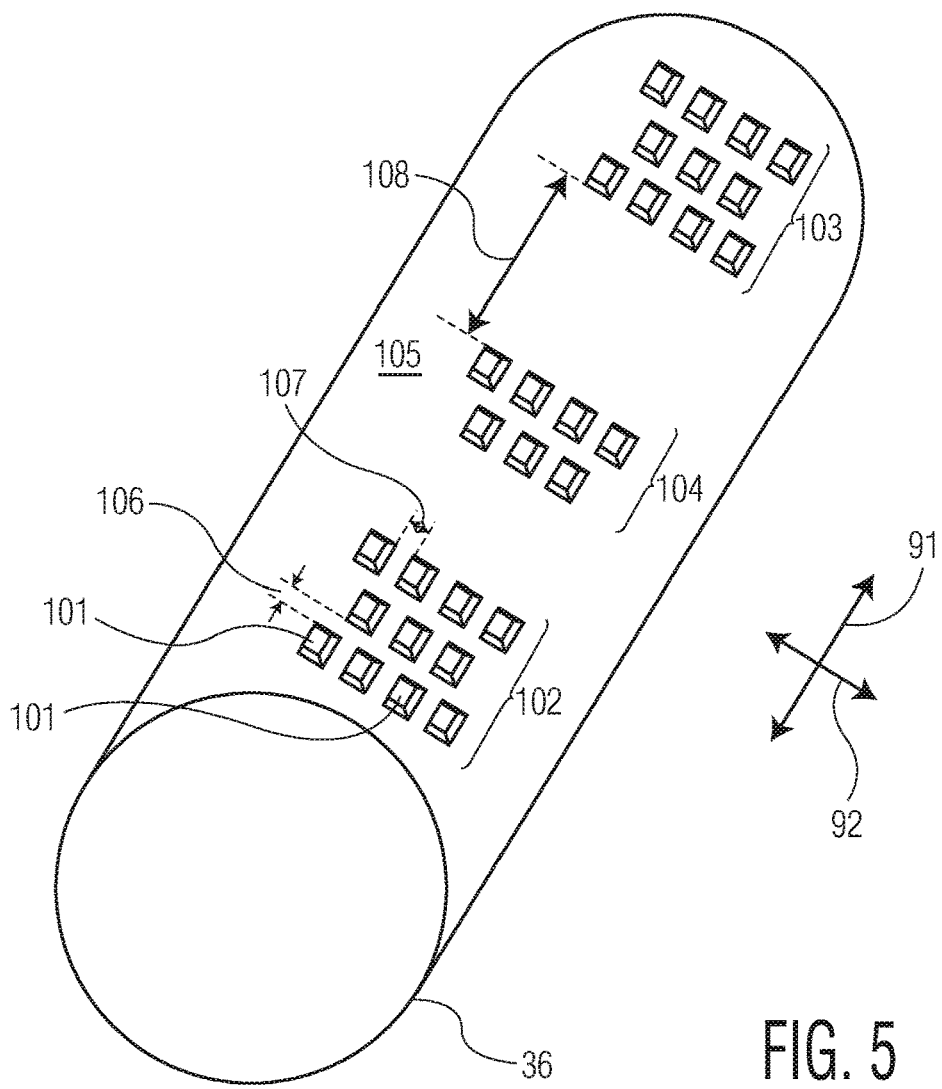
FIG. 5 is a perspective view of an exemplary pattern roll, according to aspects of the present disclosure.

FIG. 5 depicts pattern roll 36. As can be seen, pattern roll 36 comprises protrusions 101 projecting generally radially outward from a surface pattern roll 36. Additionally as can be seen, protrusions 101 are arranged in a predetermined pattern. For instance, protrusions 101 may be arranged into one or more separate groupings, such as groupings 102, 103, 104. Additionally, pattern roll 36 may comprise multiple of such groupings 102, 103, 104 spaced around the circumference of pattern roll 36. For instance, pattern roll 36 may have a first set of groupings 102, 103, 104 at a first location on the circumference of pattern roll 36, an area devoid of protrusions 101, such as area 105, and then a second set of groupings 102, 103, 104 at a second location on the circumference of pattern roll 36. The amount of area 105 between adjacent sets of groupings 102, 103, 104 may align with a machine-direction length 92 of heavy bond regions 79 such that the protrusions 101 of the different sets of groupings 102, 103, 104 align with composite elastic strands 12-14*b* within light bond regions 77. Generally, the specific arrangement of protrusions 101 on the surface of pattern roll 36 may be determined based on which specific composite elastic strands 12-14*b* are to be weakened.

In the embodiment of FIG. 5, grouping 102 may align with one or more composite elastic strands 13 located in rear waist region 72, while grouping 103 may align with one or more composite elastic strands 12 located in front waist region 71. Further, grouping 104 may be aligned with one or more composite elastic strands 14*a*, 14*b* in the crotch region. For instance, in the embodiment of FIG. 5, grouping 102 may comprise three columns of protrusions 101, which align with three composite elastic strands 13 in rear waist region 72 of elasticized web 35. Likewise, grouping 103 may comprise three columns of protrusions 101 and grouping 104 may comprise two columns of protrusions 101, which may align with three composite elastic strands 12 in front waist region 71, and two composite elastic strands 14*a*, 14*b* in the crotch region, respectively. However, it should be understood that the scope of this disclosure is not limited to the specific numbers of protrusions 101 depicted in FIG. 5. Rather, pattern rolls 36 contemplated by the present disclosure may have any suitable number of protrusions 101 and columns of protrusions 101 in order to align with any suitable number of composite elastic strands 12-14*b*. For instance, different pattern rolls contemplated by the present disclosure may have anywhere from between about 5 to about 30 columns of protrusions 101 in a grouping, which may correspond to suitable numbers of composite elastic strands 12-14*b* in the different regions of elasticized web 35. Additionally, it should be understood that the number of protrusions 101 and columns of protrusions 101 in each grouping may be less than the number of composite elastic strands 12-14*b* in each of the regions. In this manner, in at least some embodiments, less than all of composite elastic strands 12-14*b* within a region may be partially weakened. Even further, it is not necessary that pattern roll 36 include all of groupings 102, 103, and 104. Rather, patterns rolls are contemplated by the present disclosure that have any combination of groupings of protrusions 102, 103, 104, based on the specific composite elastic strands 12-14*b* to become partially weakened.

It should further be understood that the specific shape and pattern of protrusions 101 within each grouping shown in FIG. 5 is not meant to be limiting. For instance, although protrusions 101 are depicted with a generally flat-shaped top surface, other shapes for protrusions 101 may be suitable for partially weakening composite elastic strands 12-14*b* and are contemplated by the present disclosure. More specifics around suitable shapes for protrusions 101 is discussed below with respect to FIGS. 9-11. Further, although each column of protrusions 101 within a grouping is shown staggered with respect to adjacent columns, this is not required in all embodiments. In other embodiments, each of protrusions 101 within a column may align with protrusions 101 in adjacent columns. In still further embodiments, protrusions 101 may not be situated in columns at all. Rather, any pattern of protrusions 101 within a grouping may be suitable as longs as protrusions 101 align with one or more composite elastic strands 12-14*b* as elasticized web 35 is fed into nip 33.

Each of protrusions 101 situated within a grouping, such as grouping 102, may be spaced an amount from protrusions 101 in adjacent columns and from adjacent protrusions within the same column. For example, cross-direction width 106 may comprise a cross-direction 92 distance that a protrusion 101 in a first column is spaced from a protrusion 101 in an adjacent column. Some suitable values for cross-direction width 106 may be between about 0.25 inches (6.0 mm) and about 1.0 inches (25 mm). Further, machine direction distance 107 may comprise a machine-direction 91 distance between adjacent protrusions 101 within the same column. Some suitable values for machine-direction width 107 may be between about 0.125 inches (3.0 mm) and about 1.0 inches (25 mm). Each of groupings 102, 103, and 104 may additionally be spaced a predetermined distance from adjacent groupings. For instance, as seen in FIG. 5, innermost edges of protrusions 101 of grouping 103 may be spaced a cross-machine distance 108 from outer edges of protrusions 101 of grouping 104. Cross-machine distance 108 may be between about 2.0 inches (50 mm) and about 8.0 inches (203 mm). Generally, cross-machine distance 108 may be chosen such that protrusions 101 align with composite elastic strands 12-14*b* in the different regions of elasticized web 35.

Figure 6:
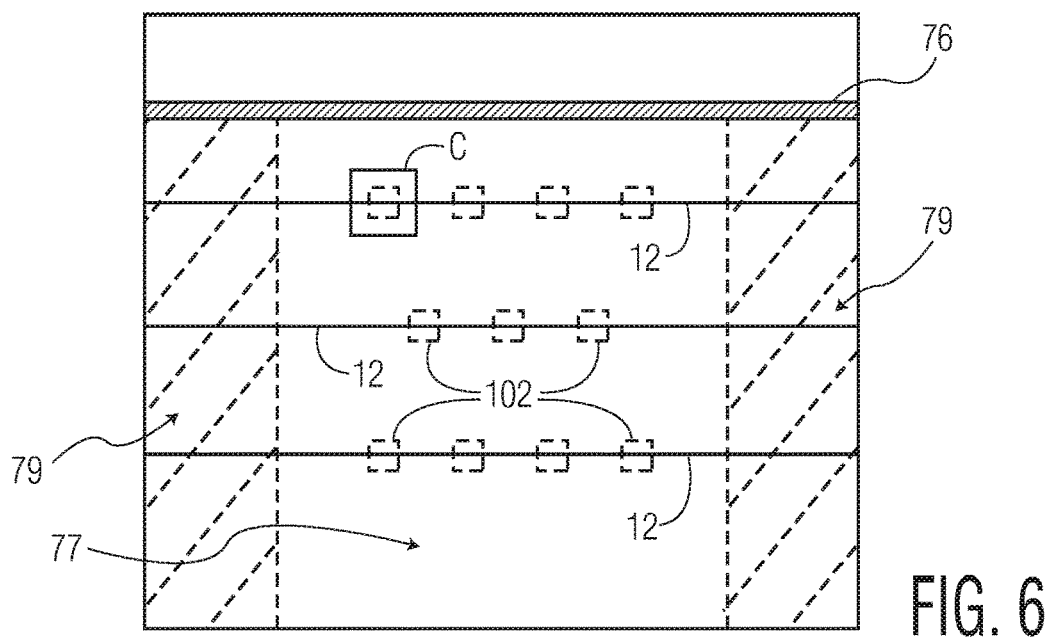
FIG. 6 is a plan view of an exemplary front waist region portion of the elasticized web of FIG. 2, detailing composite elastic strands and locations where protrusions of the pattern roll of FIG. 5 may contact the composite elastic strands.

FIG. 6 depicts a close-up of a portion of front waist region 71 of elasticized web 35 including light bond region 77, heavy bond regions 79, and composite elastic strands 12. FIG. 6 also depicts positions of where protrusions 101 may fall as elasticized web 35 progresses through nip 33, denoted by boxes 102. As can be seen each individual protrusion 101 may align with a single one of composite elastic strands 12. However, this is not required in all embodiments. In other embodiments, protrusions 101 may have a great enough cross-machine direction 91 width that a single protrusion 101 may span two or more of composite elastic strands 12. In general, each of protrusions 101 may partially weaken one or more of composite elastic strands 12 at the location where protrusions 101 contact composite elastic strands 12.

Figure 7:
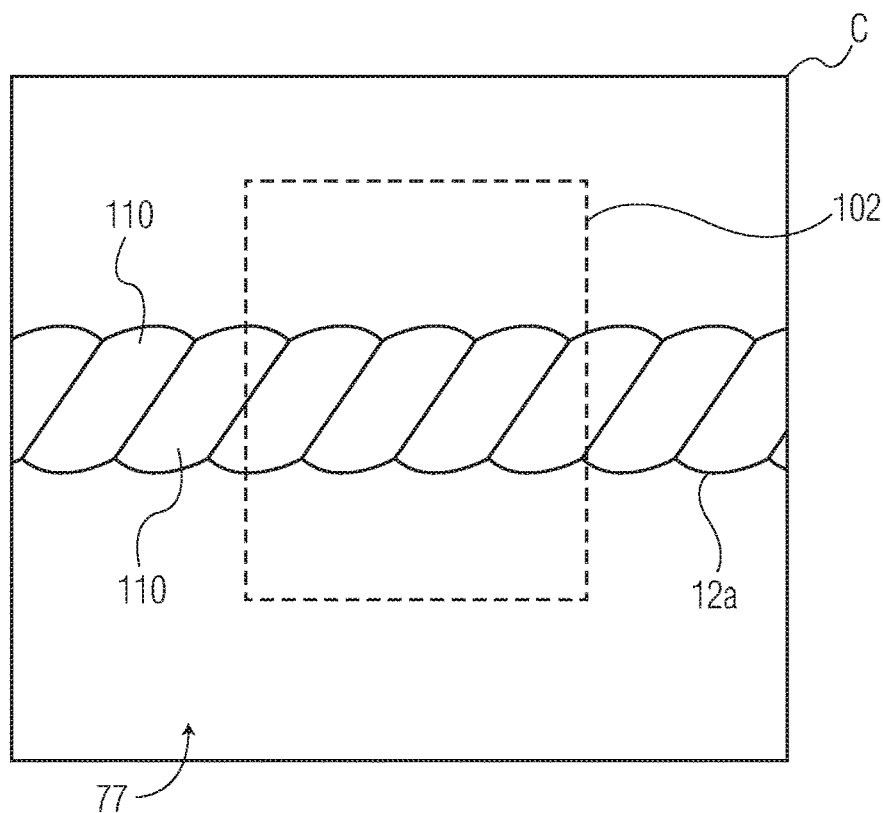
FIG. 7 is a plan view of a close-up of region C of FIG. 6.

FIG. 7 depicts a close-up of area C highlighted in FIG. 6. FIG. 7 highlights single composite elastic strand 12*a*, which can be seen is made up of a plurality of micro-strands 110 wound together to form the single composite elastic strand 12*a*. Although the micro-strands 100 are shown as wound to form composite elastic strand 12*a*, other embodiments contemplate composite elastic strands 12 formed of microstrands which have been wound, braided, or otherwise combined together.

Figure 8:
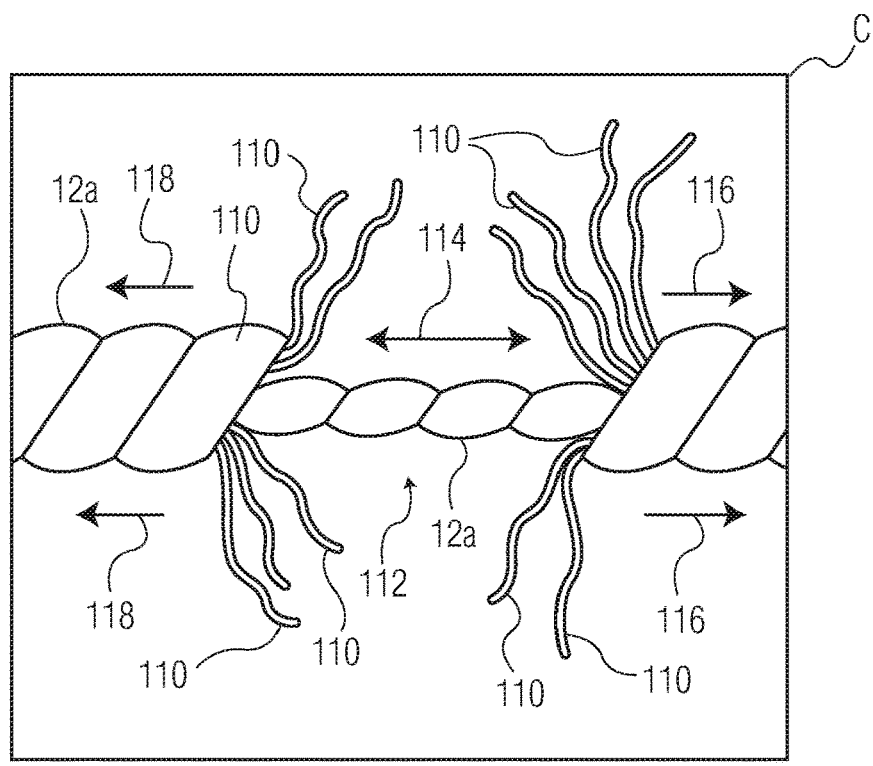
FIG. 8 is a plan view of a close-up of region C of FIG. 6 depicting a partially weakened composite elastic strands, according to aspects of the present disclosure.

When protrusions 101 contact composite elastic strands 12-14*b*, protrusions 101 may compress composite elastic strands 12-14*b* with a pressure of between about 16 psi (0.11 MPa) and about 5,800 psi (40 MPa). In other embodiments, protrusions 101 may compress composite elastic strands 12-14*b* with a pressure of between about 35 psi (0.24 MPa) and about 2,100 psi (13.8 MPa). In any case, the pressure results in portions of composite elastic strands 12-14*b* becoming partially weakened. It has been found that these pressures are enough to partially weaken composite elastic strands 12-14*b* without completely severing composite elastic strands 12-14*b*, when using protrusions having the shapes disclosed herein. FIG. 8 depicts composite elastic strand 12*a* after one of protrusions 101 of pattern roll 36 has partially weakened composite elastic strand 12*a*. As can be seen, the pressure of one of protrusions 101 compressing composite elastic strand 12*a* has severed some of micro-strands 110 of composite elastic strand 12*a*, but less than all of micro-strands 110.

Additionally, in some embodiments it may be desired that the mutilation process partially weaken one or more portions of the one or more composite elastic strands 12-14*b* without impacting body facing web 10 and/or garment facing web 11. For instance, some embodiments may partially weaken composite elastic strands 12-14*b* without cutting or otherwise forming holes or apertures in body facing web 10 and/or garment facing web 11. In such embodiments, the amount of pressure applied by protrusions 101 may be greater than the yield strength of the one or more composite elastic strands 12-14*b*, but less than the yield strength body facing web 10 and/or garment facing web 11. In different contemplated embodiments, the yield strength of the one or more composite elastic strands 12-14*b* that are to be partially weakened may be between about 0.52 MPa and about 63.0 MPa, when the one or more composite elastic strands 12-14*b* comprise urethane, while the yield strength of body facing web 10 and/or garment facing web 11 may be between about 25 MPa and about 317 MPa, when body facing web 10 and/or garment facing web 11 comprise polypropylene. Of course, although these ranges overlap, in such embodiments the specific composite elastic strands 12-14*b* may be chosen to have a yield strength less the specific chosen body facing web 10 and/or garment facing web 11 in order to ensure that the mutilation process does not impact body facing web 10 and/or garment facing web 11.

In other cases, composite elastic strand 12*a* and microstrands 110 may become deformed from the pressure applied by protrusions 101 without severing any of micro-strands 101. However, the deformation of composite elastic strand 12*a* and micro-strands 110 may still partially weaken composite elastic strand 12*a*.

In still other embodiments, additional forms of energy may be applied during the mutilation step. For instance, in addition to applying pressure to the composite elastic strands 12-14*b*, the protrusions 101 may be heated. Accordingly, the heat of the protrusions may additionally help to partially weaken the composite elastic strands 12-14*b*. In some embodiments, protrusions 101 may be heated to between about 45 degrees C. to about 150 degrees C. In further embodiments, protrusions 101 may be heated to between about 75 degrees C. to about 125 degrees C. In at least some embodiments where protrusions 101 are heated, the protrusions 101 may compress composite elastic strands 12-14*b* to a lesser degree in embodiments where protrusions 101 are not heated yet still cause a partial weakening of composite elastic strands 12-14*b*. For instance, in embodiments where protrusions are heated, the protrusions 101 may be configured to apply pressure to composite elastic strands 12-14*b* between about 25 psi (0.17 MPa) and about 1,500 psi (10.0 MPa).

In other embodiments, instead of using heat, anvil roll 47 can comprise one or more ultrasonic horns, preferably rotary ultrasonic horns; although stationary horns could also be used. The number of horns needed is determined by the width of the sonic horns compared to the cross-direction 91 spacing and the cross-direction 92 widths of groups 102, 103, 104. The use of ultrasonic horns has the advantage of applying cyclical compressive pressure many times per second, for example between about 20,000 and about 40,000, to the elasticized web 35. This cyclical compressive pressure generates heat internally in composite elastic strands 12-14*b* as well as applying compressesive pressure to composite elastic strands 12-14*b* to partially weaken the strands. The use of ultrasonic energy which both compresses and heats composite elastic strands 12-14*b* may reduce the amount of compressive pressure required to partially weaken composite elastic strands 12-14*b* and may not require any additional applied heat.

In any case, the result is a partial weakening of portions of composite elastic strands 12-14*b* that were compressed by protrusions 101. These partially weakened portions of composite elastic strands 12-14*b* may have a reduced elasticity relative to the non-weakened portions of composite elastic strands 12-14*b*. The alternating regions of weakened portions and non-weakened portions of composite elastic strands 12-14*b* results in each of composite elastic strands 12-14*b* transitioning to a new equilibrium state. After the partial weakening, the non-weakened portions of composite elastic strands 12-14*b* exert a retraction force greater than the weakened portion's ability to resist the retraction force after the weakening. Put another way, the weakened portions of composite elastic strands 12-14*b* have a reduced spring constant in comparison to the non-weakened portions of composite elastic strands 12-14*b*. As can be seen in FIG. 8, the retraction forces applied to weakened portion 112 of composite elastic strand 12*a*, as shown by arrows 116, 118, results in an elongation of the weakened portion 112 of composite elastic strand 12*a*, as shown by arrow 114. When the retraction forces of the non-weakened portions of composite elastic strand 12*a* again equal the resisting forces of weakened portion 112 of composite elastic strand 12*a*, composite elastic strand 12*a* falls into a new equilibrium state.

As described previously, because the partial weakening occurs within light bond regions 77, the weakened portions of composite elastic strands 12-14*b* elongate without pulling on body facing web 10 and/or garment facing web 11. This results in reduced bunching of the absorbent core placed over any of the weakened portions of composite elastic strands 12-14*b* and reduced ruffling of body facing web 10 and/or garment facing web 11 throughout the regions of elasticized web 35 comprising the weakened portions of composite elastic strands 12-14*b*.

Figure 9:
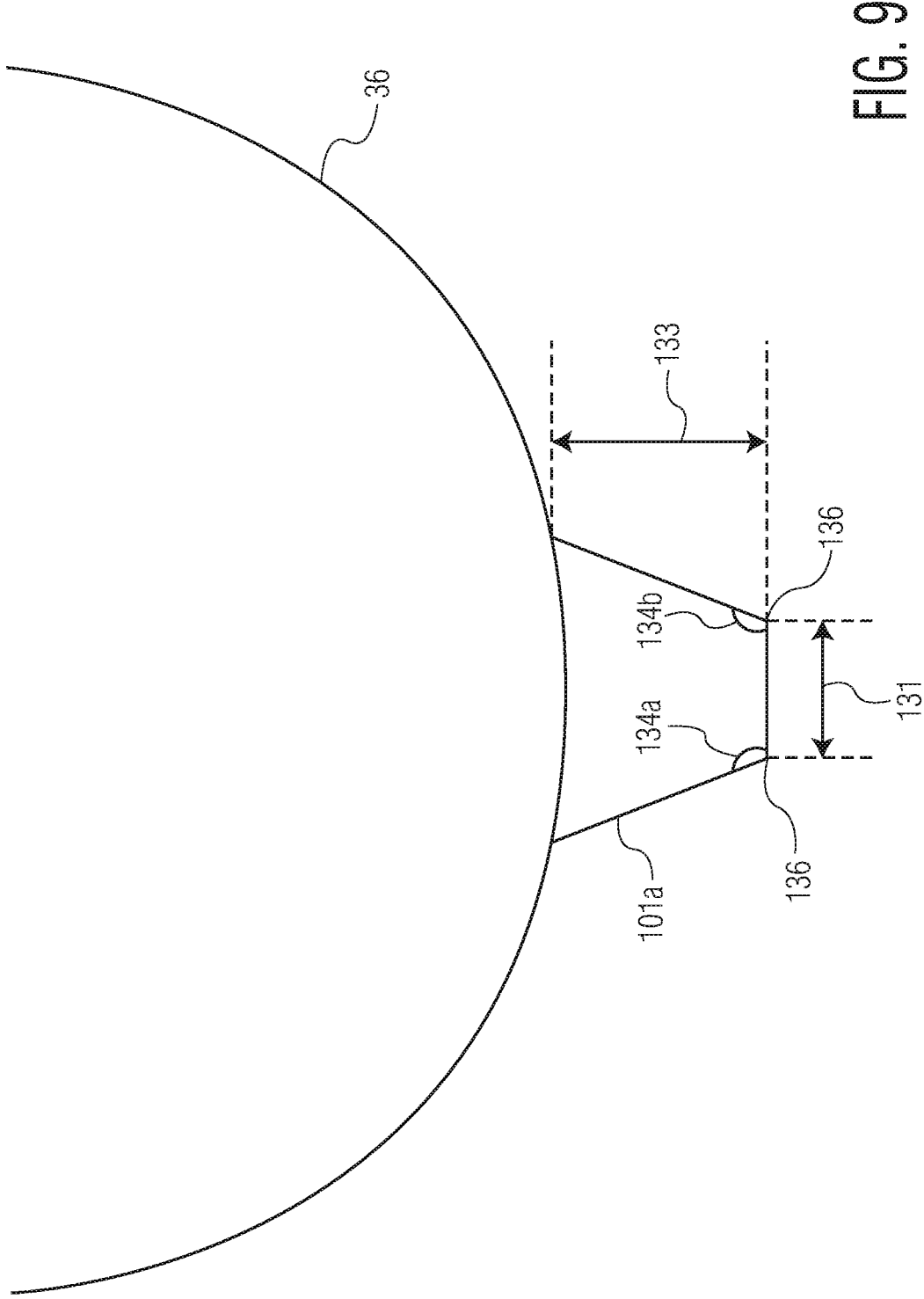
FIG. 9 is a side-view of an exemplary protrusion of the pattern roll of FIG. 5.

FIG. 9 is a side view of an exemplary protrusion of pattern roll 36 contemplated by the present disclosure, protrusion 101*a*. As can be seen in FIG. 9, protrusion 101*a* may have a generally rectangular shape. In the specific embodiment of FIG. 9, protrusion 101a may have a pyramidal shape, as protrusion 101a may taper as it extends away from pattern roll 36. In different embodiments, protrusion 101a may extend away from pattern roll 36 between about 0.060 inches (1.50 mm) and about 0.160 inches (4.0 mm). Additionally, protrusion 101a may have a width at a distal most surface from pattern roll 36 that is between about 0.25 inches (6.0 mm) and about 4 inches (102 mm). Accordingly, protrusion 101a may have angles 134a, b of between about 90 degrees and about 120 degrees. In some embodiments, angles 134a, b may be the same value, but in other embodiments angles 134a, b may be different, such as when protrusion 101a is not symmetrical. Additionally, although corners 136 are shown as relatively sharp corners, in some optional embodiments corners 136 may be beveled, chamfered, rounded, or the like.

FIG. 10 is a side view of another exemplary protrusion of pattern roll 36 contemplated by the present disclosure, protrusion 101b. As can be seen in FIG. 10, protrusion 101b may have a rounded surface most distal to pattern roll 36, as opposed to the flat distal surface of protrusion 101a. In various different embodiments according to FIG. 10, protrusion 101b may extend away from pattern roll 36 for a length 141 plus a length 143. Length 141 may be the length that protrusion 101b extends away from pattern roll 36 before beginning to curve towards tip 150, which is at points 144. Length 143 may be the length that protrusion 101b extends away from pattern roll 36 between tip 150 and points 144. Some suitable values for length 141 may be between about 0.030 inches (0.76 mm) and about 0.080 inches (2.03 mm). Some suitable values for length 143 may be between about 0.030 inches (0.76 mm) and about 0.080 inches (2.03 mm). Width 145 may represent the width of protrusion 101b between points 144. Angle 142 may be formed by an imaginary line running between tip 150 and one of points 144. Some suitable values for width 145 are between about 0.060 inches (1.52 m) and about 0.125 inches (3.18 mm). Some suitable angles for angle 142 are between about 10 degrees and about 50 degrees. In some embodiments, the distal portion of protrusion 101b may be a half-sphere. In such embodiments, angle 142 may be 45 degrees, and width 145 may represent the diameter of the distal portion of protrusion 101b. However, it should be understood that this is not necessary in all embodiments. The distal portion of protrusion 101b need not be spherical, in which case angle 142 would be greater or less than 45 degrees.

Accordingly, any of the disclosed protrusions described above may be used according to the present disclosure to partially weaken one or more of composite elastic strands 12-14b. For instance, any of the disclosed protrusions may be used with system 100, as part of pattern roll 36, for forming elasticized absorbent articles having weakened elastic portions.

Figure 11:
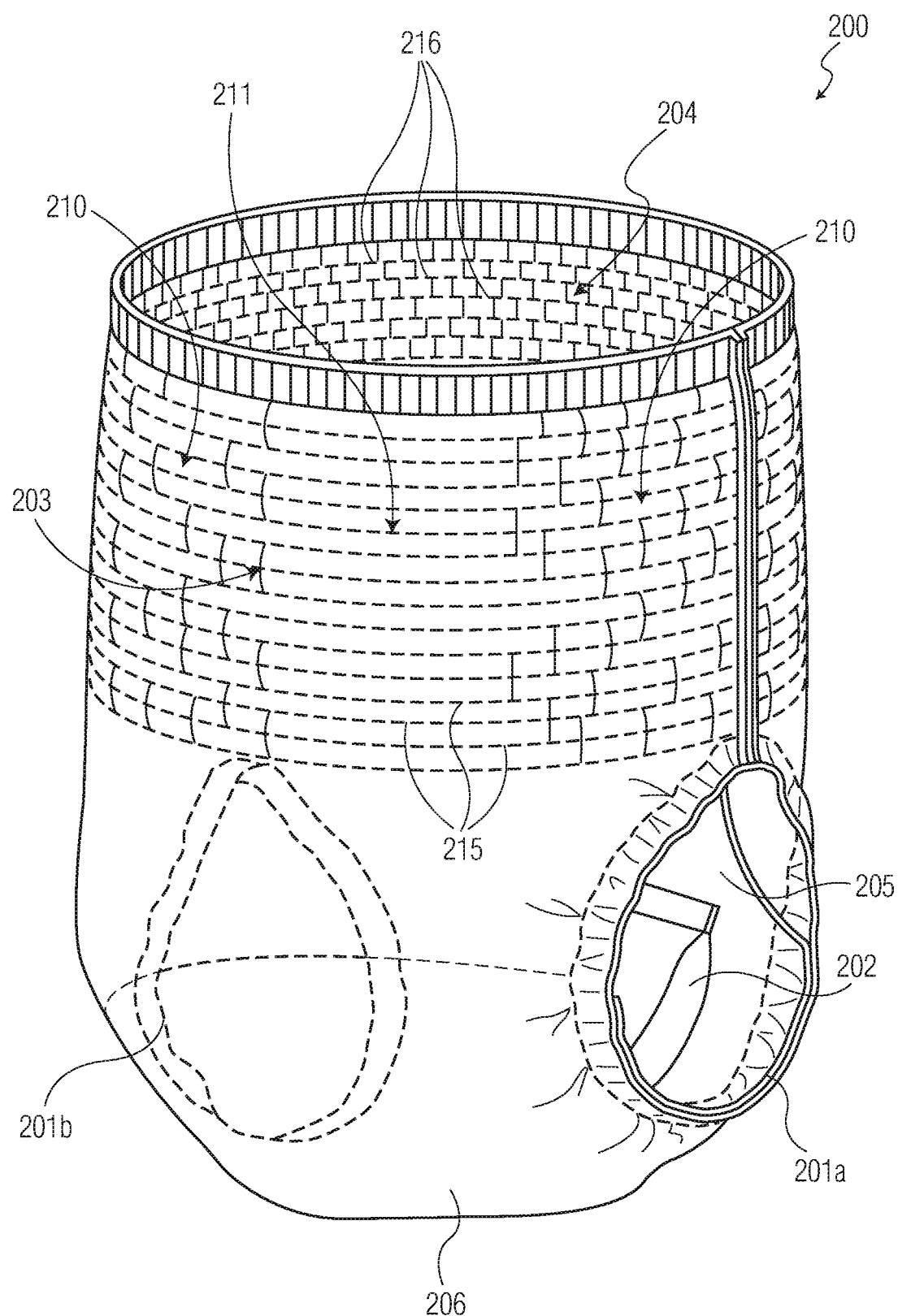
FIG. 11 is a perspective view of an exemplary elasticized absorbent pant article including weakened elastic portions, according to aspects of the present disclosure.

FIG. 11 is a perspective view of exemplary absorbent article 200. Absorbent article 200 may be, for example, a child pant absorbent article, or an adult pant absorbent article, or any other representative closed absorbent article. Absorbent article may be formed according to the process described with respect to system 100 of FIGS. 1A-1B. Accordingly, absorbent article 200 includes leg openings 201a, b, absorbent core 202, elasticized front waist panel 203, elasticized rear waist panel 204, and bodyside liner 205 and outer cover 206. Elasticized front waist panel 203 comprises composite elastic strands 215, and elasticized rear waist panel 204 comprises composite elastic strands 216.

At least some of composite elastic strands 215, 216 may include partially weakened portions. For instance, composite elastic strands 215 may include partially weakened portions at least throughout un-ruffled portion 211 situated between ruffled portions 210. As described previously, this reduction in ruffling may be due to the partial weakening of the composite elastic strands, e.g. composite elastic strands 215.

Figure 12:
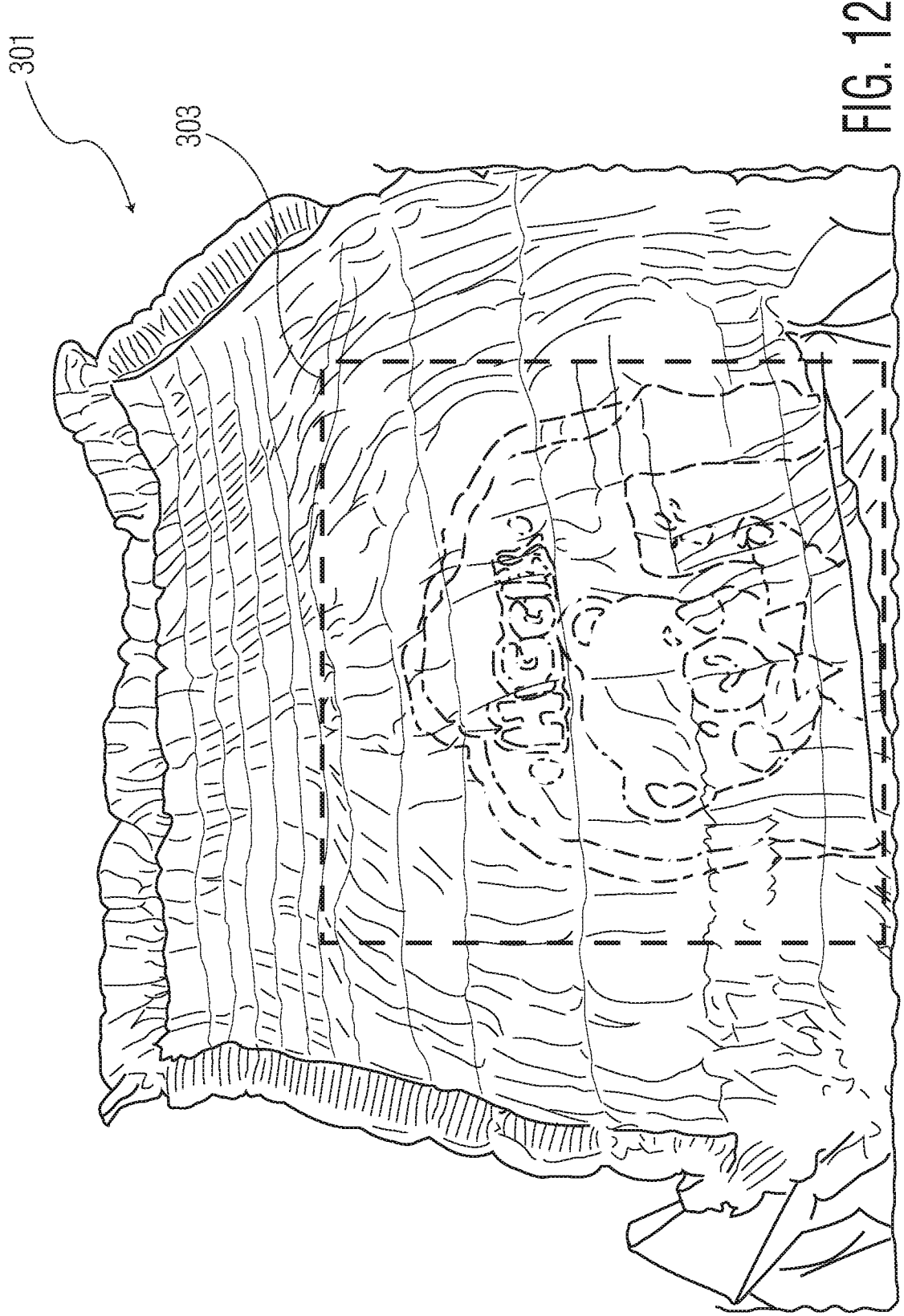
FIG. 12 is a plan view of an exemplary front waist panel of an elasticized absorbent pant article without weakened elastic portions.
Figure 13:
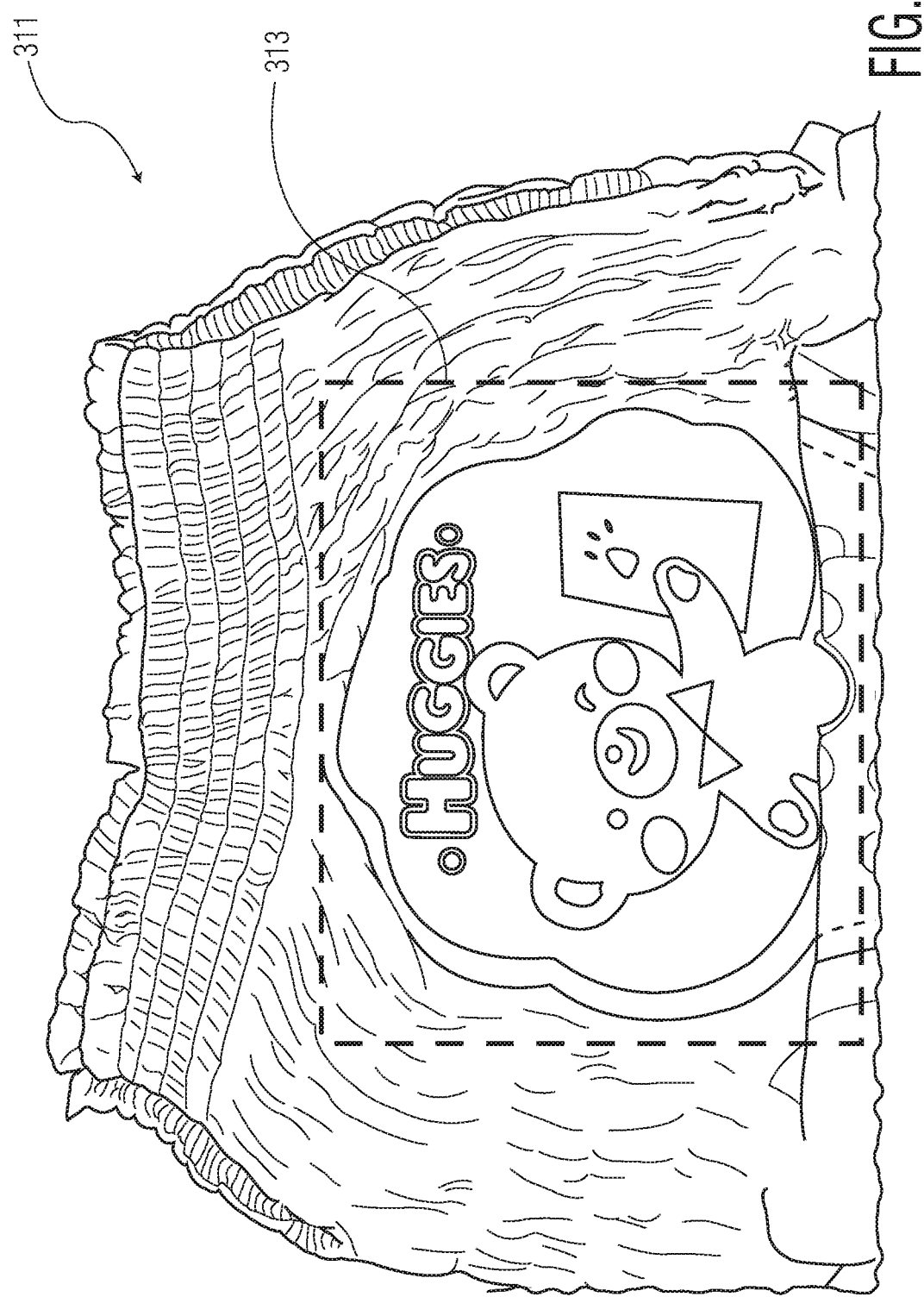
FIG. 13 is a plan view of an exemplary front waist panel of an elasticized absorbent pant article with weakened elastic portions.

FIGS. 12 and 13 are plan views of exemplary elasticized front waist panels depicting the benefits of partially weakening composite elastic strands. FIG. 12 depicts exemplary front waist panel 301, including graphic region 303, having a plurality of composite elastic strands which do not include partially weakened portions. As can be seen, the visual graphics depicted within graphic region 303 are distorted due to ruffling of front waist panel 301. In contrast, FIG. 13 depicts exemplary front waist panel 311, including graphic region 313, having a plurality of composite elastic strands which do include partially weakened portions throughout graphic region 313. As can be seen, the visual graphics are much less distorted due to the reduced ruffling of front waist panel 311 within graphic region 313.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A method of forming an elasticized portion of an absorbent article, the method comprising:
   advancing a first web of material in a machine direction;
   advancing an elastic strand in the machine direction in a stretched state;
   applying a first amount of adhesive to a first portion of at least one of the first web of material and the elastic strand;
   applying a second amount of adhesive to a second portion of at least one of the first web of material and the elastic strand;
   placing the elastic strand on a first surface of the first web of material;
   covering the elastic strand with either the first surface of the first web of material or a first surface of a second web of material to form an elasticized web, the elasticized web comprising a heavy bond region and a light bond region, the heavy bond region comprising a greater area density of adhesive than the light bond region; and
   advancing the elasticized web to a nip which applies compressive pressure to the elastic strand to partially weaken the elastic strand at least at one location within the light bond region.

2. The method of claim 1, wherein the elastic strand comprises a plurality of micro-strands, and wherein partially weakening the elastic strand comprises severing at least one of the plurality of micro-strands but less than all of the micro-strands.

3. The method of claim 1, wherein partially weakening the elastic strand comprises applying a compressive pressure of at least 0.25 MPa to the elastic strand without completely severing the elastic strand.

4. The method of claim 1, further comprises partially weakening the elastic strand at least at one location within the light bond region without forming an aperture in the first web of material or the second web of material.

5. The method of claim 1, wherein partially weakening the elastic strand at least at one location within the light bond region comprises partially weakening the elastic strand at least at five locations within the light bond region.

6. The method of claim 1, wherein after partially weakening the elastic strand at least at one location within the light bond region, the partially weakened portion of elastic strand elongates reducing ruffles in the first web of material.

7. The method of claim 1, wherein applying the first amount of adhesive to the first portion of at least one of the first web of material and the elastic strand comprises applying the first amount of adhesive to the first portion of the first web, and wherein applying the second amount of adhesive to the second portion of at least one of the first web of material and the elastic strand comprises applying the second amount of adhesive to the second portion of the first web.

8. The method of claim 1, wherein the elastic strand is a continuous elastic strand.

9. The method of claim 8, wherein partially weakening the elastic strand at least at one location within the light bond region comprises weakening the elastic strand without severing the elastic strand into separate pieces.

10. The method of claim 1, wherein the elasticized web forms an elasticized front or rear waist panel of an absorbent article.

* * * * *